(12) United States Patent
Zhu et al.

(10) Patent No.: US 8,841,272 B2
(45) Date of Patent: Sep. 23, 2014

(54) DOUBLE-STRANDED RNA-BASED NANOPARTICLES FOR INSECT GENE SILENCING

(75) Inventors: Kun Yan Zhu, Manhattan, KS (US); Xin Zhang, Manhattan, KS (US); Jianzhen Zhang, Taiyuan (CN)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 13/485,181

(22) Filed: May 31, 2012

(65) Prior Publication Data

US 2013/0137747 A1 May 30, 2013

Related U.S. Application Data

(60) Provisional application No. 61/491,729, filed on May 31, 2011.

(51) Int. Cl.
*C12N 15/11* (2006.01)
*A01N 25/00* (2006.01)
*C12N 15/113* (2010.01)

(52) U.S. Cl.
CPC ........ *C12N 15/1137* (2013.01); *C12N 2310/14* (2013.01); *C12Y 204/01016* (2013.01); *C12N 15/111* (2013.01); *C12N 2320/11* (2013.01); *C12N 2320/32* (2013.01)
USPC ........................................ 514/44 A; 424/405

(58) Field of Classification Search
None
See application file for complete search history.

(56) References Cited

U.S. PATENT DOCUMENTS

| | | | |
|---|---|---|---|
| 2004/0057977 A1* | 3/2004 | Gardner et al. | 424/410 |
| 2004/0098761 A1* | 5/2004 | Trick et al. | 800/279 |
| 2005/0226938 A1* | 10/2005 | Borbely et al. | 424/492 |
| 2006/0021087 A1* | 1/2006 | Baum et al. | 800/279 |
| 2006/0174380 A1* | 8/2006 | Carrington et al. | 800/285 |
| 2010/0015232 A1* | 1/2010 | Besenbacher et al. | 424/489 |

FOREIGN PATENT DOCUMENTS

WO    WO 2006129204 A2 * 12/2006

OTHER PUBLICATIONS

GenBank Accession # AY056833 (Oct. 2001).*
Katas et al, Development and characterisation of chitosan nanoparticles for siRNA delivery, 2006, Journal of Controlled Release, 115: 216-225.*
X. Zhang, et. al., Chitosan/double-stranded RNA nanoparticle-mediated RNA interference to silence chitin synthase genes through larval feeding in the African malaria mosquito (*Anopheles gambiae*), copyright 2010 The Authors, Insect Molecular Biology, copyright 2010 The Royal Entomological Society, 19(5), 683-693 (11 pages).
Jianzhen Zhang, et al., "Characterization of a chitin synthase cDNA and its increased mRNA level associated with decreased chitin synthesis in Anopheles quadrimaculatus exposed to diflubenzuron", Insect Biochemistry and Molecular Biology 36 (2006) 712-725, copyright 2006 Elsevier Ltd. (14 pages).

* cited by examiner

*Primary Examiner* — Tracy Vivlemore
*Assistant Examiner* — Kate Poliakova
(74) *Attorney, Agent, or Firm* — Hovey Williams LLP

(57) ABSTRACT

Nanoparticles for insect RNAi via oral delivery are provided, along with methods of silencing a target gene in a target insect using RNAi are provided. The nanoparticles comprise a polymer matrix and insect dsRNA. The dsRNA comprises at least one sequence having a region of complementarity substantially complementary to at least a portion of an mRNA transcript of the target gene. Insect baits comprising the nanoparticles are also provided. Methods of screening target gene functions are also provided using the methods disclosed herein.

15 Claims, 6 Drawing Sheets

Table I

| Application of primers | Gene | Primer name | Primer sequence (5'-3') | Length (base) | Tm (°C) |
|---|---|---|---|---|---|
| dsRNA synthesis | AgCHS1-f1 | F | TAATACGACTCACTATAGGGTGAAACGCACATCTTCTCG (SEQ ID NO: 5) | 40 | 65.5 |
| | | R | TAATACGACTCACTATAGGGAGCGTCAGCAGGTAGGTGTT (SEQ ID NO: 6) | 40 | 67.6 |
| | AgCHS1-f12 | F | TAATACGACTCACTATAGGGGCAAAACGACGGACG (SEQ ID NO: 7) | 36 | 66.7 |
| | | R | TAATACGACTCACTATAGGGTGCGCAATACGTGCC (SEQ ID NO: 8) | 36 | 66.7 |
| | AgCHS2-f1 | F | TAATACGACTCACTATAGGGACACATCGAGTGGTGGTTCA (SEQ ID NO: 9) | 40 | 66.5 |
| | | R | TAATACGACTCACTATAGGGTTGTGCTGGTAGAGAATGCG (SEQ ID NO: 10) | 40 | 66.5 |
| | AgCHS2-f2 | F | TAATACGACTCACTATAGGGGCCAGCGCCGAAAAG (SEQ ID NO: 11) | 35 | 66.8 |
| | | R | TAATACGACTCACTATAGGGTCCGACAGATCGAGCG (SEQ ID NO: 12) | 36 | 66.7 |
| | GFP | F | TAATACGACTCACTATAGGGTGGAGAGGGTGAAGG (SEQ ID NO: 13) | 36 | 66.7 |
| | | R | TAATACGACTCACTATAGGGGGCAGATTGTGTGGAC (SEQ ID NO: 14) | 37 | 66.7 |
| qPCR analysis | AgCHS1 | F | ACGAGCGCGACTTCCTCAC (SEQ ID NO: 15) | 19 | 55.4 |
| | | R | GAGTCGCGCAACTCCTTGAG (SEQ ID NO: 16) | 20 | 55.9 |
| | AgCHS2 | F | CACCAGCAACGCCATCATC (SEQ ID NO: 17) | 19 | 53.2 |
| | | R | GAACACCAGCAGCAGAGTAAC (SEQ ID NO: 18) | 21 | 54.4 |
| | AgRPS3 | F | GCTGGGCATCAAGGTCAAG (SEQ ID NO: 19) | 19 | 55.4 |
| | | R | ATCTCATCCTTCGGCTCAAC (SEQ ID NO: 20) | 20 | 54.4 |

Fig. 1

SEQUENCE LISTING

<160> NUMBER OF SEQ ID NOS: 20

<210> SEQ ID NO 1
<211> LENGTH: 5156
<212> TYPE: DNA
<213> ORGANISM: Anopheles gambiae

<400> SEQUENCE: 1

```
cgaaccctgg tcgcatgctg tcgcgtcgtc tggcggttgg tgtctcccgt gtgcttgagc      60
tgtgctgtgt gtaaagacgt ggtgggtgaa cgaaacgaaa agaaaaaaag aacgaatgtg     120
cgtcgactga accgttgtcg tcgtcgtcaa tgattgggcc gccgttcagt ggttgcgtaa     180
gataacggct cgccgagcg tgtaaggaga tcgagagtgg aagaaaacag cacaagagag      240
ccacagagcg ctgggacgga gggttgaatt tcggcattga gcggcttttg gataaggcag     300
gcggcataat cccctcccc cagtaccgtg cagcagtaaa agggcaggct gaagcagaca      360
gctgggctgg agtgatcaac tgttgactgg agccgtttgt agaggcttaa gccgagaaga    420
tgtctgctat cagacatcga cctctggcaa atggtcccaa cgagagcgat gacaactttt     480
ccgacgacga aagcacgccc ttgacgcatg atatctatgg aggaagtcag cgcaccgtgc     540
aggaaacgaa aggatgggac gtcttccggg atcctccgat caaggaggat acgggctcga     600
tggcggacca ggcctgcctc gatctgacga tcaagatcct gaagatcttc gcctacctca     660
tcaccttcgt gatcgtgctg ctcggtggcg tcgtggccaa gggctgcgta ctgttcatgt     720
cgtcgcagtt gcgccgcgac cggaagatta cctactgcaa ccgtgatctg cgcgggaca     780
aatcgttcat cgtgtcgctg ccggaggagg agcggatagc gtggatgtgg cgctgatga     840
tagccgttcgc cgtgcccgag atcggcacct tcatccggtc gacgcgtatc tgcttcttca     900
agtcgatgaa gaaaccgctc aaatcgcact ttctgctcgt cttcctgatg gaatcgttcc     960
acacgatcgg gttggtgctg ctgttcttcg tcgtgctgcc ggaggtggac tccgtcaagg    1020
gtgcaatgct gaccaactgt ctgtgtgtta taccgggtat gctgggtctg ttttcgcgca    1080
ccaacaagga aggcaaacgg gcggtaaaat cgatcgtcga tttggctgcg attgcggccc    1140
aaattaccgg cttcatcgtc tggccgctgc tcgagaatcg tcccgtgctt tggttgattc    1200
cagtgtcagc tcttctaaca tcttgcggct ggtgggaaaa ctacgtctca ccacagagcc    1260
ccttctcgtt cgtacgatcg cttggtcgcg tgaaggagga cctgaagcaa acgcgctact    1320
ttacctacat gttcctttcg gtttggaaga ttctgctgct gttctgcttc gtaagcgtaa    1380
tactgtttgt gcggggtgat gaggtggcca atcttttctc gctcttcggg gctgggtacg    1440
gcccacacaa gatcgtcgta gaggaggtag ctctaccgtt cagttccgcc ctgcccgatt    1500
tggtcgaagc tgcgcaagcg gtagacacga tcgacatcga tgctgcctac aacacggtca    1560
cgtacgtgct catcatccag atattggccg cctatctgtg ctacattttc ggcaaattcg    1620
cgtgcaaaat ccttattcaa ggtttcagtt acgctttccc ggtgaatcta accgtgccgg    1680
ttgcgatttc gctgctcatt gctgcgtgcg gtattcgcaa cgatgatccg tgcttcttcc    1740
acggctccat tcccgactat ctgttcttcg agagtccgcc cgtcttccgg ctgaacgatt    1800
tcgcctcacg ccagatggcg tgggcctggt tgctgtggtt gctctcgcaa acctggatca    1860
cgctgcacat ctgacgcccc aagtgcgaac gtttggccaa cacggagaag ctgttcgtga    1920
cgccgatgta cagcgcgctg ctgatcgacc agtcgatggc gatgaaccgc cggcgcgacg    1980
atcaggccga cgtgaagacg gaggatctgg cggagatcga aaggagaag ggcgacgagt     2040
actacgaaac gatctcggtg cacacggacg gttcggccct gccgcgcccg agcgtgaaat    2100
```

-continued

```
cctccgatca catcacgcgc atctacgcct gcgccacgct ttggcacgaa acgaaggagg    2160
agatgatggt gttcctcaag tcgatcatgc gtatggacga ggatcagtgc gcacgacgcg    2220
tggcacagaa gtatctgcgt atcgtcgatc ccgattacta cgagtttgaa acgcacatct    2280
tcttcgatga cgcgttcgaa atttcggacc acagcgacga ggacattcag tgtaatcggt    2340
tcgtgaagat tcttgtcgac accatcgacg aagctgcctc ggaagtgcat cagaccaaca    2400
ttcgattgag accgcccaaa aagtacccaa caccgtacgg tggacgactg gtgtggacgc    2460
tgcccggtaa aacgaagatg attgcccacc tgaaggacaa ggatcgcatc cggcaccgta    2520
agcgttggtc tcaggtcatg tacatgtact atctgctcgg ccaccggctg atggagctgc    2580
cgatttccgt cgaccgtaag gaggtgatgg cggaaaacac ctacctgctg acgctggacg    2640
gtgatatcga ctttaacccg agccgccgtga cgctgctgat cgatttgatg aagaagaata    2700
agaacctggg tgcggcttgt gggcgtattc atccgatcgg ctcgggaccg atggtgtggt    2760
accagaagtt cgagtacgct atcggccatt ggctgcagaa ggcaacggag cacatgatcg    2820
gttgtgtact ttgtagtcct ggttgctttt cactgttcag aggaaagggt ctgatggacg    2880
acaatgtaat gcgcaagtac acgacacgct cggacgaggc acggcactac gtgcagtacg    2940
atcagggcga ggatcgttgg ctgtgtacgc tgctgctgca gcgtggctat cgcgtcgagt    3000
actcggctgc ctcggacgcc tacacccact gcccggaagg gttcaacgag ttctacaacc    3060
agcgtcgccg ctgggtaccg tccaccattg ccaacatcat ggacctgctg atggactaca    3120
ggcgcacgat caagatcaac gacaacatct cgctgctgta catcttctac cagatgatgc    3180
tgatgggcgg tacgatcctt ggccccggta cgattttcct catgttggtg ggtgcgttcg    3240
tggccgcgtt caagatcgac aactggacct cgttctacta caacatcata ccgatcatgc    3300
tgttcatgct ggtgtgcttc acctgcaagt ccaacataca gctgctggtc gcgcagatac    3360
tgtccaccgt gtacgcattg atcatgatgg ccgtcattgt cggtaccgcg ttacagctcg    3420
gcgaggacgg catcggttca ccgtcggcca ttttcctgat agcaatgaca gggtccttct    3480
ttatagcggc ctgtctgcat ccgcaagagt tttggtgcat cgcgtccggc atcatctatc    3540
tgctgtcgat tccgtccatg tacctgctgc tcatcctcta ctccatcatc aatctgaacg    3600
tggtctcgtg gggtacgcgc gaggtggtag cgaagaagac gaagaaagaa atggagcagg    3660
aaaagaagga cgccgaggag gccgccaaac gggcgaagca aaagtcgctg cttggcttcc    3720
tgcagggtgg cgttgggaat gggtcggatg aggagggctc gatcgacatc tcgatcgcgg    3780
gcctgttccg ctgtttgctc tgcacacacg gcaaaacgac ggacgagaag gcgcagctga    3840
ttcacattgc cgatgcgctg gacgccatta cgaagaagat tgagaatctg gaaaagcaca    3900
tcgacccgca cggacatcat acgcgcaagc gcactgcgtc ggcggggtcg aaggatcacc    3960
atctcggctc ggtggcggag gatacggagg acgatgatga ggatgaagat tcggagactt    4020
cgacgctgca gcgcgacgag cgcgacttcc tcaccaaccc gtactggatc gaggatccgg    4080
atctgaagaa gggcgaggtg gactttattt ccagcaccga gatccagttc tggaaggacc    4140
tgatcgataa gtacctatac ccgatcgatc aaaacaagga ggaacaggca cgtattgcgc    4200
acgatctcaa ggagttgcgc gactccgccg tgttcggttt catcatgatc aatgcactgt    4260
ttgtgctgat cgtattcttg ctacagctca acaaggacaa catccacgtc aagtggccgt    4320
tgggtgttaa aactaacatt acctatgatg aagccacgca agaggtgcac atctccaagg    4380
agtatctgca gctggaaccg atcggtctgg tgtttgtgtt cttcttcgcc ctgattctga    4440
tcattcagtt tgtggcaatg atgttccatc ggttcggcac actgtcgcac attctggcct    4500
```

-continued

```
cgaccgagct caactgggcc tgcaacaaga agccggagga gctttcgcag gatgctctca    4560
tagacaagca cgctgttgag atagtcaaga atttgcaacg actgcaaggc atcgatggag    4620
attacgacaa tgattcgggc agcggtccgg accgcatcgc acgccgccgc acgatccaga    4680
acctcgaaaa ggcacggcaa ccgcgccgac agattggtac gctcgatgtg gcgttcaaga    4740
agcggttcct gaagctgacg gccgacgaga acaataccgc cacccccgatc cttacccgcc    4800 ggatgacgat gcgccgcgaa acgatccgtg cgctggaggt gcgcaagaac tcggtgatgg    4860
cggagcggcg caagtcgcaa atgcagacgc tcggggccaa caacgagtac ggcattacgg    4920
gtgtgccgaa tggaaataat aacgccccac cgaggccgac gcgtacttcg aacgctggcg    4980
ttagcgtgaa ggacatcttc aacgtgaacg gtggtcccgg cggtgaaatc tacggtgtca    5040
ctggccaggt gaaccaagcg tacgaaccgg taattgagga tgacgatcgc aactcgctgc    5100
gcctgcagcc ccgcaaccag gtcacctggg gtaacaatgg taacgcacgg ttgtga        5156
```

<210> SEQ ID NO 2
<211> LENGTH: 1566
<212> TYPE: PRT
<213> ORGANISM: Anopheles gambiae

<400> SEQUENCE: 2

```
Met Ser Ala Ile Arg His Arg Pro Leu Ala Asn Gly Pro Asn Glu Ser
1               5                   10                  15

Asp Asp Asn Phe Ser Asp Glu Ser Thr Pro Leu Thr His Asp Ile
            20                  25                  30

Tyr Gly Gly Ser Gln Arg Thr Val Gln Glu Thr Lys Gly Trp Asp Val
        35                  40                  45

Phe Arg Asp Pro Pro Ile Lys Glu Asp Thr Gly Ser Met Ala Asp Gln
    50                  55                  60

Ala Cys Leu Asp Leu Thr Ile Lys Ile Leu Lys Ile Phe Ala Tyr Leu
65                  70                  75                  80

Ile Thr Phe Val Ile Val Leu Leu Gly Gly Val Val Ala Lys Gly Cys
                85                  90                  95

Val Leu Phe Met Ser Ser Gln Leu Arg Arg Asp Arg Lys Ile Thr Tyr
            100                 105                 110

Cys Asn Arg Asp Leu Ala Arg Asp Lys Ser Phe Ile Val Ser Leu Pro
        115                 120                 125

Glu Glu Glu Arg Ile Ala Trp Met Trp Ala Leu Met Ile Ala Phe Ala
    130                 135                 140

Val Pro Glu Ile Gly Thr Phe Ile Arg Ser Thr Arg Ile Cys Phe Phe
145                 150                 155                 160

Lys Ser Met Lys Lys Pro Leu Lys Ser His Phe Leu Leu Val Phe Leu
                165                 170                 175

Met Glu Ser Phe His Thr Ile Gly Leu Val Leu Leu Phe Phe Val Val
            180                 185                 190

Leu Pro Glu Val Asp Ser Val Lys Gly Ala Met Leu Thr Asn Cys Leu
        195                 200                 205

Cys Val Ile Pro Gly Met Leu Gly Leu Phe Ser Arg Thr Asn Lys Glu
    210                 215                 220

Gly Lys Arg Ala Val Lys Ser Ile Val Asp Leu Ala Ala Ile Ala Ala
225                 230                 235                 240

Gln Ile Thr Gly Phe Ile Val Trp Pro Leu Leu Glu Asn Arg Pro Val
                245                 250                 255
```

-continued

Leu Trp Leu Ile Pro Val Ser Ala Leu Leu Thr Ser Cys Gly Trp Trp
        260                 265                 270

Glu Asn Tyr Val Ser Pro Gln Ser Pro Phe Ser Phe Val Arg Ser Leu
        275                 280                 285

Gly Arg Val Lys Glu Asp Leu Lys Gln Thr Arg Tyr Phe Thr Tyr Met
        290                 295                 300

Phe Leu Ser Val Trp Lys Ile Leu Leu Leu Phe Cys Phe Val Ser Val
305                 310                 315                 320

Ile Leu Phe Val Arg Gly Asp Glu Val Ala Asn Leu Phe Ser Leu Phe
                325                 330                 335

Gly Ala Gly Tyr Gly Pro His Lys Ile Val Glu Glu Val Ala Leu
        340                 345                 350

Pro Phe Ser Ser Ala Leu Pro Asp Leu Val Glu Ala Ala Gln Ala Val
        355                 360                 365

Asp Thr Ile Asp Ile Asp Ala Ala Tyr Asn Thr Val Thr Tyr Val Leu
        370                 375                 380

Ile Ile Gln Ile Leu Ala Ala Tyr Leu Cys Tyr Ile Phe Gly Lys Phe
385                 390                 395                 400

Ala Cys Lys Ile Leu Ile Gln Gly Phe Ser Tyr Ala Phe Pro Val Asn
                405                 410                 415

Leu Thr Val Pro Val Ala Ile Ser Leu Leu Ile Ala Ala Cys Gly Ile
        420                 425                 430

Arg Asn Asp Asp Pro Cys Phe Phe His Gly Ser Ile Pro Asp Tyr Leu
                435                 440                 445

Phe Phe Glu Ser Pro Pro Val Phe Arg Leu Asn Asp Phe Ala Ser Arg
        450                 455                 460

Gln Met Ala Trp Ala Trp Leu Leu Trp Leu Leu Ser Gln Thr Trp Ile
465                 470                 475                 480

Thr Leu His Ile Trp Thr Pro Lys Cys Glu Arg Leu Ala Asn Thr Glu
                485                 490                 495

Lys Leu Phe Val Thr Pro Met Tyr Ser Ala Leu Leu Ile Asp Gln Ser
        500                 505                 510

Met Ala Met Asn Arg Arg Arg Asp Asp Gln Ala Asp Val Lys Thr Glu
        515                 520                 525

Asp Leu Ala Glu Ile Glu Lys Glu Lys Gly Asp Glu Tyr Tyr Glu Thr
        530                 535                 540

Ile Ser Val His Thr Asp Gly Ser Ala Leu Pro Arg Pro Ser Val Lys
545                 550                 555                 560

Ser Ser Asp His Ile Thr Arg Ile Tyr Ala Cys Ala Thr Leu Trp His
                565                 570                 575

Glu Thr Lys Glu Glu Met Met Val Phe Leu Lys Ser Ile Met Arg Met
        580                 585                 590

Asp Glu Asp Gln Cys Ala Arg Arg Val Ala Gln Lys Tyr Leu Arg Ile
        595                 600                 605

Val Asp Pro Asp Tyr Tyr Glu Phe Glu Thr His Ile Phe Asp Asp
        610                 615                 620

Ala Phe Glu Ile Ser Asp His Ser Asp Glu Asp Ile Gln Cys Asn Arg
625                 630                 635                 640

Phe Val Lys Ile Leu Val Asp Thr Ile Asp Glu Ala Ala Ser Glu Val
                645                 650                 655

His Gln Thr Asn Ile Arg Leu Arg Pro Pro Lys Lys Tyr Pro Thr Pro
        660                 665                 670

```
Tyr Gly Gly Arg Leu Val Trp Thr Leu Pro Gly Lys Thr Lys Met Ile
            675                 680                 685

Ala His Leu Lys Asp Lys Asp Arg Ile Arg His Arg Lys Arg Trp Ser
690                 695                 700

Gln Val Met Tyr Met Tyr Tyr Leu Leu Gly His Arg Leu Met Glu Leu
705                 710                 715                 720

Pro Ile Ser Val Asp Arg Lys Glu Val Met Ala Glu Asn Thr Tyr Leu
                725                 730                 735

Leu Thr Leu Asp Gly Asp Ile Asp Phe Asn Pro Ser Ala Val Thr Leu
                740                 745                 750

Leu Ile Asp Leu Met Lys Lys Asn Lys Asn Leu Gly Ala Ala Cys Gly
                755                 760                 765

Arg Ile His Pro Ile Gly Ser Gly Pro Met Val Trp Tyr Gln Lys Phe
            770                 775                 780

Glu Tyr Ala Ile Gly His Trp Leu Gln Lys Ala Thr Glu His Met Ile
785                 790                 795                 800

Gly Cys Val Leu Cys Ser Pro Gly Cys Phe Ser Leu Phe Arg Gly Lys
                805                 810                 815

Gly Leu Met Asp Asp Asn Val Met Arg Lys Tyr Thr Thr Arg Ser Asp
                820                 825                 830

Glu Ala Arg His Tyr Val Gln Tyr Asp Gln Gly Glu Asp Arg Trp Leu
            835                 840                 845

Cys Thr Leu Leu Leu Gln Arg Gly Tyr Arg Val Glu Tyr Ser Ala Ala
850                 855                 860

Ser Asp Ala Tyr Thr His Cys Pro Glu Gly Phe Asn Glu Phe Tyr Asn
865                 870                 875                 880

Gln Arg Arg Arg Trp Val Pro Ser Thr Ile Ala Asn Ile Met Asp Leu
                885                 890                 895

Leu Met Asp Tyr Arg Arg Thr Ile Lys Ile Asn Asp Asn Ile Ser Leu
                900                 905                 910

Leu Tyr Ile Phe Tyr Gln Met Met Leu Met Gly Gly Thr Ile Leu Gly
            915                 920                 925

Pro Gly Thr Ile Phe Leu Met Leu Val Gly Ala Phe Val Ala Ala Phe
            930                 935                 940

Lys Ile Asp Asn Trp Thr Ser Phe Tyr Tyr Asn Ile Ile Pro Ile Met
945                 950                 955                 960

Leu Phe Met Leu Val Cys Phe Thr Cys Lys Ser Asn Ile Gln Leu Leu
                965                 970                 975

Val Ala Gln Ile Leu Ser Thr Val Tyr Ala Leu Ile Met Met Ala Val
                980                 985                 990

Ile Val Gly Thr Ala Leu Gln Leu  Gly Glu Asp Gly Ile  Gly Ser Pro
            995                 1000                1005

Ser Ala  Ile Phe Leu Ile Ala  Met Thr Gly Ser Phe  Phe Ile Ala
         1010                1015                1020

Ala Cys  Leu His Pro Gln Glu  Phe Trp Cys Ile Ala  Ser Gly Ile
         1025                1030                1035

Ile Tyr  Leu Leu Ser Ile Pro  Ser Met Tyr Leu Leu  Leu Ile Leu
         1040                1045                1050

Tyr Ser  Ile Ile Asn Leu Asn  Val Val Ser Trp Gly  Thr Arg Glu
         1055                1060                1065

Val Val  Ala Lys Lys Thr Lys  Lys Glu Met Glu Gln  Glu Lys Lys
         1070                1075                1080
```

-continued

Asp Ala Glu Glu Ala Ala Lys Arg Ala Lys Gln Lys Ser Leu Leu
1085                1090                1095

Gly Phe Leu Gln Gly Gly Val Gly Asn Gly Ser Asp Glu Glu Gly
1100                1105                1110

Ser Ile Asp Ile Ser Ile Ala Gly Leu Phe Arg Cys Leu Leu Cys
1115                1120                1125

Thr His Gly Lys Thr Thr Asp Glu Lys Ala Gln Leu Ile His Ile
1130                1135                1140

Ala Asp Ala Leu Asp Ala Ile Thr Lys Lys Ile Glu Asn Leu Glu
1145                1150                1155

Lys His Ile Asp Pro His Gly His His Thr Arg Lys Arg Thr Ala
1160                1165                1170

Ser Ala Gly Ser Lys Asp His His Leu Gly Ser Val Ala Glu Asp
1175                1180                1185

Thr Glu Asp Asp Asp Glu Asp Glu Asp Ser Glu Thr Ser Thr Leu
1190                1195                1200

Gln Arg Asp Glu Arg Asp Phe Leu Thr Asn Pro Tyr Trp Ile Glu
1205                1210                1215

Asp Pro Asp Leu Lys Lys Gly Glu Val Asp Phe Ile Ser Ser Thr
1220                1225                1230

Glu Ile Gln Phe Trp Lys Asp Leu Ile Asp Lys Tyr Leu Tyr Pro
1235                1240                1245

Ile Asp Gln Asn Lys Glu Glu Gln Ala Arg Ile Ala His Asp Leu
1250                1255                1260

Lys Glu Leu Arg Asp Ser Ala Val Phe Gly Phe Ile Met Ile Asn
1265                1270                1275

Ala Leu Phe Val Leu Ile Val Phe Leu Leu Gln Leu Asn Lys Asp
1280                1285                1290

Asn Ile His Val Lys Trp Pro Leu Gly Val Lys Thr Asn Ile Thr
1295                1300                1305

Tyr Asp Glu Ala Thr Gln Glu Val His Ile Ser Lys Glu Tyr Leu
1310                1315                1320

Gln Leu Glu Pro Ile Gly Leu Val Phe Val Phe Phe Phe Ala Leu
1325                1330                1335

Ile Leu Ile Ile Gln Phe Val Ala Met Met Phe His Arg Phe Gly
1340                1345                1350

Thr Leu Ser His Ile Leu Ala Ser Thr Glu Leu Asn Trp Ala Cys
1355                1360                1365

Asn Lys Lys Pro Glu Glu Leu Ser Gln Asp Ala Leu Ile Asp Lys
1370                1375                1380

His Ala Val Glu Ile Val Lys Asn Leu Gln Arg Leu Gln Gly Ile
1385                1390                1395

Asp Gly Asp Tyr Asp Asn Asp Ser Gly Ser Gly Pro Asp Arg Ile
1400                1405                1410

Ala Arg Arg Arg Thr Ile Gln Asn Leu Glu Lys Ala Arg Gln Pro
1415                1420                1425

Arg Arg Gln Ile Gly Thr Leu Asp Val Ala Phe Lys Lys Arg Phe
1430                1435                1440

Leu Lys Leu Thr Ala Asp Glu Asn Asn Thr Ala Thr Pro Ile Leu
1445                1450                1455

Thr Arg Arg Met Thr Met Arg Arg Glu Thr Ile Arg Ala Leu Glu
1460                1465                1470

| | | | | | | | | | | |
|---|---|---|---|---|---|---|---|---|---|---|
| Val | Arg | Lys | Asn | Ser | Val | Met | Ala | Glu | Arg | Arg | Lys | Ser | Gln | Met |
| | 1475 | | | | 1480 | | | | | 1485 |

Gln Thr Leu Gly Ala Asn Asn Glu Tyr Gly Ile Thr Gly Val Pro
    1490                1495                1500

Asn Gly Asn Asn Asn Ala Pro Pro Arg Pro Thr Arg Thr Ser Asn
    1505                1510                1515

Ala Gly Val Ser Val Lys Asp Ile Phe Asn Val Asn Gly Gly Pro
    1520                1525                1530

Gly Gly Glu Ile Tyr Gly Val Thr Gly Gln Val Asn Gln Ala Tyr
    1535                1540                1545

Glu Pro Val Ile Glu Asp Asp Asp Arg Asn Ser Leu Arg Leu Gln
    1550                1555                1560

Pro Arg Asn
    1565

<210> SEQ ID NO 3
<211> LENGTH: 5408
<212> TYPE: DNA
<213> ORGANISM: Anopheles gambiae

<400> SEQUENCE: 3

```
atgaagaaca acgccaccat gaactacttc accgaatcgt ccgacgagga tgacgaggag      60
acggtcatga tcaaaaaagt gcagcaggac aacaagctat gggactcgtt ccaggatccg     120
cccgtaccgc agacatccgg ttccgccgcc agccgggagt atctgctcgt gttcatcaaa     180
gggctgaagg tgtttaccta catctttgtg tttctcgtca tactggccag tgcgtgcttt     240
gccaagatgt ccttcctgct gatggtgtcc aacgtaaagg acgggaccaa gaatcgttac     300
tgtgacgtgc ggcagcccga caaacagttc gaagcgtaca ttccactcga gcagcgagta     360
gcctggatgt gggcgattgt gttctcgttt gccgtgccgg aggtcggaac ctttatccgg     420
gcggcacgca tctgcttctt caaaaacatc ccgcgaccgt cctggggcca gctgttgatg     480
gttacgatta tggagagctt ccacgtgatt gggttggcaa ttttgacgtt tttagtgtac     540
cccaacctgg acgtcgttaa ggccgcgatg ctgtcgaact gtgtctgcct agtgcctgcc     600
atcggtggac tgctatcccg ttcgcacaaa gagtccaagc tggccttcaa gtacgtcttc     660
gatctgcttg cgatcagtgc gcagcttacc ggttacgttg tgtggccact gctcagtaac     720
cagtttgagc tgtggttcat cccggggagcc atctttctca tatcctgcca ctggtgggag     780
aattacttat cgcagaaaag tctatttcga ccaatcgcat cattcgctgc tatacgcgaa     840
aaattaaccg acaaccggta ccaaacgtat ctactgatcg cgccgtacaa aatcttccta     900
tttctcgggg cctgcatcta tctctccggc caaacggtga ccgattttt cggactgttt     960
gatagtggct ggggtaatca caccatcaca gtacgcgaga tggaagccgt gttgaacgaa    1020
aagtttcccg acctctcgtc catcacgtcc gatctggagg aacacgaaat tttccccacc    1080
agcaacgcca tcatctggac cacggtcaca catatcctgt gtgcgtatct gtgctacatc    1140
ttcagcaaat ttgcgtgcaa atccagattc aaagtttctc catggcgtt cccgatcaat    1200
ctcgcggtac cggtcacagt tactctgctg ctggtgttct gtggtctgcg agaggcggat    1260
gtctgtgcgt tcgacaatat cctgcctgac tacatcttct ccgtatgcc tccgatctac    1320
tacctcttcg attacgttgt caacgagttt tcttggctct ggttgctatg gctgctctcg    1380
caaacctgga tcacccgcca tctgtggatg gcaaagagcg atcgaacgc atcgaccgag    1440
aaacttttcg taacacctat gtacaacagc ctactgatag accagagcgt tgccatgaat    1500
```

```
cgccgacggg aggatcagga agatttcgtt aagaaaattg atatggttaa agtgaaagat    1560
acagaaaagg cgaacgaaat tgatgccaag gcacacgagg gaaaggatga caagatcaaa    1620
ccgtacgatc gcatcccgca gatattcatt tgtgcaacca tgtggcacga aaacaaggag    1680
gaactgatgg agttcttgaa atccatccta cgactggatg aagatcagtg tgccaggcgg    1740
atggcgatga acacatacag caaacaagga tgatatg atcctgacta ttacgatctc    1800
gaaactcaca ttttcttcga cgacgcgttc gtaaatgata atccaagtg cgagagtgcc    1860 gatgcctcac cgctcaattc ctacgtaaag acgctaatca accacatcga agaggcggcc    1920
ctggaagtgt acaaaaccaa gatgcgcgta tatccgccca ccaagatcgt cactccatac    1980
ggtggccgat tgatctggac actgccggga aggacgaaaa tgattgcaca cctcaaggac    2040
aaaaacaaga tccgcacaa gaagcgctgg tcacaggtta tgtacatgta ctacctgctc    2100
ggctaccgaa tcatgcagct gaacacatcg cccgagcgaa agatggtcat cgcccaaaac    2160
acctacctgt tggcactgga cggggacatt gatttccaac cgaacgccgt ctccctgctt    2220
gtcggacgaa tgaaggtcga tccggacctg ggtgctgcct gtggacgcat tcatccggtc    2280
ggcacgggac cgatggtttg gtatcagatc ttcgagtacg ccatcggaca ttggctgcag    2340
aaggctaccg agcacgtgat tggctgcgtg ctgtgttcgc ccggttgttt ctcgctcttc    2400
cgcggtcgtg ccctgatgga aaactccgtc atgaagaagt acactaccaa gtcggaccag    2460
gcacgccact acgtccagta cgatcagggt gaggatcgat ggctgtgcac cctgttgttg    2520
aagcaaaagt ccgcgtcga gtattcggcc gcctcggacg cttatacgca cgccccggaa    2580
gggtttaacg agttctacaa ccagcgccgt cgctgggttc cgtccaccat gccaacatc    2640 ttcgatctgc tggcggatgc gaaacgggtc gtcaagacga acaacagcat ctccatgccg    2700
tacatcatct accagtgcat gctcatgttc ggcacaatcc tcggcccggg cacgatcttt    2760
ctcatgatgg tgggtgccct ggtggccgtg tttcgtatcg acatttggac ctccttcctg    2820
tggaacggcg ttccgctcgc cgggtttatg ccatctgct actggatgaa gcaaaagtat    2880
caactgatag cggccttctt catctcggcc atctattcgc tcgtcatgat ggccgtgctg    2940
gtcggtatcg tggtgcaggt gatggaggac ggtatacttg cgccgtcgtc cgtgttcttt    3000
ctcgccgtcg cgctgcagat cgtcatcacc ggtgtgctgc atccacagga aatggaagcg    3060
ctgccggccg gcctggtgta ctacatcacc attccctcca tgtacatgtt gctcgtgatc    3120
tactccgtat tcaacatgaa cgatgtgtcc tggggaacgc gtgaaaaccc cgttgatgca    3180
gcgaaaaagg caccaccgcc ggtagcggcc ccggcaggaa agatgcaaaa atatattgggc    3240 tatctccgct cgcccgataa ggaggaggac ggttccattg acatctccat caatggcctg    3300
ttccgatgtc tgctctgtac gcacccaaag gccagcgccg aaaaggagca aatcgcacaa    3360
attgcggcat cgctcagcga aataagtgta aaaatgaagg cactggaaat gaaattaacc    3420
ggcaacgtca gcgtaatgag atcagacgac gaagatgatg acatcggtag tctcgatatg    3480
catcgtccgg aaggtaaccg tggcccatcc tcgccatcct ccacctcggg cgccgcctcc    3540
ccgatccaga cggtgaaaaa tgattccctc gaagagcccg agaagcagat taactatctg    3600
ccggattggt tgtacgacgt ggatttgaaa acggcgaca ctgagacgat ctccgcctcg    3660
gaggagcaat tctggattga gctgatcgag aagtatctga agccgctcga tctgtcggaa    3720
aagcagaagg aagagatgaa gtcacagctc aaaggtctac gcgatctggc cgtgtttgcc    3780
ttcgtcatgg cgaacgcact gtttgtgctg gtaatctttc tgctgcagct gaaaaaacag    3840
gagctacaca tcgagtggtg gttcaacgtg aagaacaaga tcagctttga cgaaagcacg    3900
```

-continued

| | |
|---|---|
| gtcgagatca tgatccggcg cgagtacctg gagctcgaac cgatcggttt ggtgtttgtg | 3960 |
| atgttcttcg gtttgattct catcattcag tttgtggcca tgctgatgca tcggttcggt | 4020 |
| accatctccc agattcttgc ctccaccgag ctgaactggt actgttcgaa gaaggctaag | 4080 |
| gatatgtcac tcgatgcgga actgcgcgag aatgcggtcg aaattgcacg tcgactgcag | 4140 |
| cgccccaaac cgcagtggga cgaggaagat ctagaggacg agcagaaagc tattggacgt | 4200 |
| cgcgacacga tccatcgcat tctctaccag cacaaaaaca gcaggactg gagcaacctg | 4260 |
| gaggctaact tcaagcgcaa ctactacaag gagggcgaac tggaccttgg ccatcggctt | 4320 |
| acgctcagcc ggaaaacact caacgtgctc gatacacgcc gtaaatcgat ggccgaacag | 4380 |
| cgcaagatcc gcaaatcgat catccggggc cagaatccgt acgattcggc cggagatctt | 4440 |
| tggtatccgg acgaaccgcc cggccagcaa ccatctcccg ctcgcggtc ctacaacggc | 4500 |
| cagatgggcg gtggaggcgc caatcggaag cgcagcagtg ccaccaacaa tggcggtgga | 4560 |
| cgccaatcat ccaacaacgg gctcggcgcc ggaggtcgca ccaactttgc ctaccaagtg | 4620 |
| gacgacgatt tcgacgacaa ctactccgat gatgatgccc gcgaggaaat gcagtaccgt | 4680 |
| cgaccgacgg tcgagctcga gatggccgaa cgagcgaacc ggccacccaa aaatcgcaag | 4740 |
| agccgtgttg ccttcgcctg accatgatgg cgatccacag gccacacaac tgtggcgaaa | 4800 |
| gcggggcacg agacaccgaa tgtaacaaat tactgctcat gaggttcctg ttgagttgac | 4860 |
| gccaaacttc cgacactgac tgtgggatgt ggttttcgat ggtccgcgca accacttgcg | 4920 |
| cgctccagct tggttcttgg gtggaagcta aaggagtggc cccaacatcg aagaacaaaa | 4980 |
| acactcaacc gttcagcgca caaaaaagac actcccaaaa cgaaactttc cttcgctgca | 5040 |
| agatgagctg gcatggttga agcaacacca gaacaacaaa aagccccggt agcttctcgg | 5100 |
| cgagagatga tgaaggaacc ggaagattat agctcagcgc gagtggaacg agtgctttcg | 5160 |
| gttaagcgta cccggcgtac cagaagcgtc gagcagtttc tcattttcac aaactatttg | 5220 |
| actgcgggcc aacaccgaga caccatagtc atacacacac acacacacac atccacaccc | 5280 |
| acaacacgtc ctcgtcctgg tgcaccaccg tttaccaaca ccactctcgg aacgattttt | 5340 |
| cactgtacga tccaaggaag gaaatttaat cacttctaca aatgattatc ataataaact | 5400 |
| tttcttct | 5408 |

<210> SEQ ID NO 4
<211> LENGTH: 1253
<212> TYPE: PRT
<213> ORGANISM: Anopheles gambiae

<400> SEQUENCE: 4

```
Met Glu Ala Val Leu Asn Glu Lys Phe Pro Asp Leu Ser Ser Ile Thr
1               5                   10                  15

Ser Asp Leu Glu Glu His Glu Ile Phe Pro Thr Ser Asn Ala Ile Ile
            20                  25                  30

Trp Thr Thr Val Thr His Ile Leu Cys Ala Tyr Leu Cys Tyr Ile Phe
        35                  40                  45

Ser Lys Phe Ala Cys Lys Ile Gln Ile Gln Ser Phe Ser Met Ala Phe
    50                  55                  60

Pro Ile Asn Leu Ala Val Pro Val Thr Val Thr Leu Leu Leu Val Phe
65                  70                  75                  80

Cys Gly Leu Arg Glu Ala Asp Val Cys Ala Phe Asp Asn Ile Leu Pro
                85                  90                  95
```

-continued

```
Asp Tyr Ile Phe Phe Arg Met Pro Pro Ile Tyr Tyr Leu Phe Asp Tyr
            100                 105                 110

Val Val Asn Glu Phe Ser Trp Leu Trp Leu Trp Leu Leu Ser Gln
        115                 120                 125

Thr Trp Ile Thr Arg His Leu Trp Met Ala Lys Ser Asp Arg Asn Ala
    130                 135                 140

Ser Thr Glu Lys Leu Phe Val Thr Pro Met Tyr Asn Ser Leu Leu Ile
145                 150                 155                 160

Asp Gln Ser Val Ala Met Asn Arg Arg Arg Glu Asp Gln Glu Asp Phe
                165                 170                 175

Val Lys Lys Ile Asp Met Val Lys Val Lys Asp Thr Glu Lys Ala Asn
            180                 185                 190

Glu Ile Asp Ala Lys Ala His Glu Gly Lys Asp Asp Lys Ile Lys Pro
        195                 200                 205

Tyr Asp Arg Ile Pro Gln Ile Phe Ile Cys Ala Thr Met Trp His Glu
    210                 215                 220

Asn Lys Glu Glu Leu Met Glu Phe Leu Lys Ser Ile Leu Arg Leu Asp
225                 230                 235                 240

Glu Asp Gln Cys Ala Arg Arg Met Ala Met Lys His Ile Gln Ala Asn
                245                 250                 255

Lys Asp Asp Ile Asp Pro Asp Tyr Tyr Asp Leu Glu Thr His Ile Phe
            260                 265                 270

Phe Asp Asp Ala Phe Val Asn Asp Lys Ser Lys Cys Glu Ser Ala Asp
        275                 280                 285

Ala Ser Pro Leu Asn Ser Tyr Val Lys Thr Leu Ile Asn His Ile Glu
    290                 295                 300

Glu Ala Ala Leu Glu Val Tyr Lys Thr Lys Met Arg Val Tyr Pro Pro
305                 310                 315                 320

Thr Lys Ile Val Thr Pro Tyr Gly Gly Arg Leu Ile Trp Thr Leu Pro
                325                 330                 335

Gly Arg Thr Lys Met Ile Ala His Leu Lys Asp Lys Asn Lys Ile Arg
            340                 345                 350

His Lys Lys Arg Trp Ser Gln Val Met Tyr Met Tyr Tyr Leu Leu Gly
        355                 360                 365

Tyr Arg Ile Met Gln Leu Asn Thr Ser Pro Glu Arg Lys Met Val Ile
    370                 375                 380

Ala Gln Asn Thr Tyr Leu Leu Ala Leu Asp Gly Asp Ile Asp Phe Gln
385                 390                 395                 400

Pro Asn Ala Val Ser Leu Leu Val Gly Arg Met Lys Val Asp Pro Asp
                405                 410                 415

Leu Gly Ala Ala Cys Gly Arg Ile His Pro Val Gly Thr Gly Pro Met
            420                 425                 430

Val Trp Tyr Gln Ile Phe Glu Tyr Ala Ile Gly His Trp Leu Gln Lys
        435                 440                 445

Ala Thr Glu His Val Ile Gly Cys Val Leu Cys Ser Pro Gly Cys Phe
    450                 455                 460

Ser Leu Phe Arg Gly Arg Ala Leu Met Glu Asn Ser Val Met Lys Lys
465                 470                 475                 480

Tyr Thr Thr Lys Ser Asp Gln Ala Arg His Tyr Val Gln Tyr Asp Gln
                485                 490                 495

Gly Glu Asp Arg Trp Leu Cys Thr Leu Leu Leu Lys Gln Lys Phe Arg
            500                 505                 510
```

-continued

Val Glu Tyr Ser Ala Ala Ser Asp Ala Tyr Thr His Ala Pro Glu Gly
            515                 520                 525

Phe Asn Glu Phe Tyr Asn Gln Arg Arg Trp Val Pro Ser Thr Ile
530                 535                 540

Ala Asn Ile Phe Asp Leu Leu Ala Asp Ala Lys Arg Val Val Lys Thr
545                 550                 555                 560

Asn Asn Ser Ile Ser Met Pro Tyr Ile Ile Tyr Gln Cys Met Leu Met
                565                 570                 575

Phe Gly Thr Ile Leu Gly Pro Gly Thr Ile Phe Leu Met Met Val Gly
            580                 585                 590

Ala Leu Val Ala Val Phe Arg Ile Asp Ile Trp Thr Ser Phe Leu Trp
            595                 600                 605

Asn Gly Val Pro Leu Ala Gly Phe Met Ala Ile Cys Tyr Trp Met Lys
            610                 615                 620

Gln Lys Tyr Gln Leu Ile Ala Ala Phe Phe Ile Ser Ala Ile Tyr Ser
625                 630                 635                 640

Leu Val Met Met Ala Val Leu Val Gly Ile Val Val Gln Val Met Glu
                645                 650                 655

Asp Gly Ile Leu Ala Pro Ser Ser Val Phe Phe Leu Ala Val Ala Leu
            660                 665                 670

Gln Ile Val Ile Thr Gly Val Leu His Pro Gln Glu Met Glu Ala Leu
            675                 680                 685

Pro Ala Gly Leu Val Tyr Tyr Ile Thr Ile Pro Ser Met Tyr Met Leu
            690                 695                 700

Leu Val Ile Tyr Ser Val Phe Asn Met Asn Asp Val Ser Trp Gly Thr
705                 710                 715                 720

Arg Glu Asn Pro Val Asp Ala Ala Lys Lys Ala Pro Pro Val Ala
                725                 730                 735

Ala Pro Ala Gly Lys Met Gln Lys Ile Leu Gly Tyr Leu Arg Ser Pro
            740                 745                 750

Asp Lys Glu Glu Asp Gly Ser Ile Asp Ile Ser Ile Asn Gly Leu Phe
            755                 760                 765

Arg Cys Leu Leu Cys Thr His Pro Lys Ala Ser Ala Glu Lys Glu Gln
770                 775                 780

Ile Ala Gln Ile Ala Ala Ser Leu Ser Glu Ile Ser Val Lys Met Lys
785                 790                 795                 800

Ala Leu Glu Met Lys Leu Thr Gly Asn Val Ser Val Met Arg Ser Asp
            805                 810                 815

Asp Glu Asp Asp Asp Ile Gly Ser Leu Asp Met His Arg Pro Glu Gly
            820                 825                 830

Asn Arg Gly Pro Ser Ser Pro Ser Ser Thr Ser Gly Ala Ala Ser Pro
            835                 840                 845

Ile Gln Thr Val Lys Asn Asp Ser Leu Glu Glu Pro Glu Lys Gln Ile
            850                 855                 860

Asn Tyr Leu Pro Asp Trp Leu Tyr Asp Val Asp Leu Lys Asn Gly Asp
865                 870                 875                 880

Thr Glu Thr Ile Ser Ala Ser Glu Glu Gln Phe Trp Ile Glu Leu Ile
                885                 890                 895

Glu Lys Tyr Leu Lys Pro Leu Asp Leu Ser Glu Lys Gln Lys Glu Glu
            900                 905                 910

Met Lys Ser Gln Leu Lys Gly Leu Arg Asp Leu Ala Val Phe Ala Phe
            915                 920                 925

```
Val Met Ala Asn Ala Leu Phe Val Leu Val Ile Phe Leu Leu Gln Leu
930                 935                 940

Lys Lys Gln Glu Leu His Ile Glu Trp Trp Phe Asn Val Lys Asn Lys
945                 950                 955                 960

Ile Ser Phe Asp Glu Ser Thr Val Glu Ile Met Ile Arg Arg Glu Tyr
                965                 970                 975

Leu Glu Leu Glu Pro Ile Gly Leu Val Phe Val Met Phe Phe Gly Leu
                980                 985                 990

Ile Leu Ile Ile Gln Phe Val Ala Met Leu Met His Arg Phe Gly Thr
                995                 1000                1005

Ile Ser Gln Ile Leu Ala Ser Thr Glu Leu Asn Trp Tyr Cys Ser
    1010                1015                1020

Lys Lys Ala Lys Asp Met Ser Leu Asp Ala Glu Leu Arg Glu Asn
    1025                1030                1035

Ala Val Glu Ile Ala Arg Arg Leu Gln Arg Pro Lys Pro Gln Trp
    1040                1045                1050

Asp Glu Glu Asp Leu Glu Asp Glu Gln Lys Ala Ile Gly Arg Arg
    1055                1060                1065

Asp Thr Ile His Arg Ile Leu Tyr Gln His Lys Asn Lys Gln Asp
    1070                1075                1080

Trp Ser Asn Leu Glu Ala Asn Phe Lys Arg Asn Tyr Tyr Lys Glu
    1085                1090                1095

Gly Glu Leu Asp Leu Gly His Arg Leu Thr Leu Ser Arg Lys Thr
    1100                1105                1110

Leu Asn Val Leu Asp Thr Arg Arg Lys Ser Met Ala Glu Gln Arg
    1115                1120                1125

Lys Ile Arg Lys Ser Ile Ile Arg Gly Gln Asn Pro Tyr Asp Ser
    1130                1135                1140

Ala Gly Asp Leu Trp Tyr Pro Asp Glu Pro Pro Gly Gln Gln Pro
    1145                1150                1155

Ser Pro Gly Ser Arg Ser Tyr Asn Gly Gln Met Gly Gly Gly Gly
    1160                1165                1170

Ala Asn Arg Lys Arg Ser Ser Ala Thr Asn Asn Gly Gly Gly Arg
    1175                1180                1185

Gln Ser Ser Asn Asn Gly Leu Gly Ala Gly Gly Arg Thr Asn Phe
    1190                1195                1200

Ala Tyr Gln Val Asp Asp Asp Phe Asp Asp Asn Tyr Ser Asp Asp
    1205                1210                1215

Asp Ala Arg Glu Glu Met Gln Tyr Arg Arg Pro Thr Val Glu Leu
    1220                1225                1230

Glu Met Ala Glu Arg Ala Asn Arg Pro Pro Lys Asn Arg Lys Ser
    1235                1240                1245

Arg Val Ala Phe Ala
    1250

<210> SEQ ID NO 5
<211> LENGTH: 40
<212> TYPE: DNA
<213> ORGANISM: Artificial Sequence
<220> FEATURE:
<223> OTHER INFORMATION: Primer for dsRNA synthesis

<400> SEQUENCE: 5
taatacgact cactataggg tgaaacgcac atcttcttcg                    40
```

```
<210> SEQ ID NO 6
<211> LENGTH: 40
<212> TYPE: DNA
<213> ORGANISM: Artificial Sequence
<220> FEATURE:
<223> OTHER INFORMATION: Primer for dsRNA synthesis

<400> SEQUENCE: 6
taatacgact cactataggg agcgtcagca ggtaggtgtt                          40

<210> SEQ ID NO 7
<211> LENGTH: 36
<212> TYPE: DNA
<213> ORGANISM: Artificial Sequence
<220> FEATURE:
<223> OTHER INFORMATION: Primer for dsRNA synthesis

<400> SEQUENCE: 7
taatacgact cactataggg ggcaaaacga cggacg                              36

<210> SEQ ID NO 8
<211> LENGTH: 36
<212> TYPE: DNA
<213> ORGANISM: Artificial Sequence
<220> FEATURE:
<223> OTHER INFORMATION: Primer for dsRNA synthesis

<400> SEQUENCE: 8
taatacgact cactataggg gtgcgcaata cgtgcc                              36

<210> SEQ ID NO 9
<211> LENGTH: 40
<212> TYPE: DNA
<213> ORGANISM: Artificial Sequence
<220> FEATURE:
<223> OTHER INFORMATION: Primer for dsRNA synthesis

<400> SEQUENCE: 9
taatacgact cactataggg acacatcgag tggtggttca                          40

<210> SEQ ID NO 10
<211> LENGTH: 40
<212> TYPE: DNA
<213> ORGANISM: Artificial Sequence
<220> FEATURE:
<223> OTHER INFORMATION: Primer for dsRNA synthesis

<400> SEQUENCE: 10
taatacgact cactataggg ttgtgctggt agagaatgcg                          40

<210> SEQ ID NO 11
<211> LENGTH: 35
<212> TYPE: DNA
<213> ORGANISM: Artificial Sequence
<220> FEATURE:
<223> OTHER INFORMATION: Primer for dsRNA synthesis

<400> SEQUENCE: 11
taatacgact cactataggg gccagcgccg aaaag                               35

<210> SEQ ID NO 12
<211> LENGTH: 36
<212> TYPE: DNA
<213> ORGANISM: Artificial Sequence
<220> FEATURE:
<223> OTHER INFORMATION: Primer for dsRNA synthesis
```

```
<400> SEQUENCE: 12
taatacgact cactataggg tccgacagat cgagcg                               36

<210> SEQ ID NO 13
<211> LENGTH: 36
<212> TYPE: DNA
<213> ORGANISM: Artificial Sequence
<220> FEATURE:
<223> OTHER INFORMATION: Primer for dsRNA synthesis

<400> SEQUENCE: 13
taatacgact cactataggg gtggagaggg tgaagg                               36

<210> SEQ ID NO 14
<211> LENGTH: 37
<212> TYPE: DNA
<213> ORGANISM: Artificial Sequence
<220> FEATURE:
<223> OTHER INFORMATION: Primer for dsRNA synthesis

<400> SEQUENCE: 14
taatacgact cactataggg gggcagattg tgtggac                              37

<210> SEQ ID NO 15
<211> LENGTH: 19
<212> TYPE: DNA
<213> ORGANISM: Artificial Sequence
<220> FEATURE:
<223> OTHER INFORMATION: Primer for qPCR

<400> SEQUENCE: 15
acgagcgcga cttcctcac                                                  19

<210> SEQ ID NO 16
<211> LENGTH: 20
<212> TYPE: DNA
<213> ORGANISM: Artificial Sequence
<220> FEATURE:
<223> OTHER INFORMATION: Primer for qPCR

<400> SEQUENCE: 16
gagtcgcgca actccttgag                                                 20

<210> SEQ ID NO 17
<211> LENGTH: 19
<212> TYPE: DNA
<213> ORGANISM: Artificial Sequence
<220> FEATURE:
<223> OTHER INFORMATION: Primer for qPCR

<400> SEQUENCE: 17
caccagcaac gccatcatc                                                  19

<210> SEQ ID NO 18
<211> LENGTH: 21
<212> TYPE: DNA
<213> ORGANISM: Artificial Sequence
<220> FEATURE:
<223> OTHER INFORMATION: Primer for qPCR

<400> SEQUENCE: 18
gaacaccagc agcagagtaa c                                               21
```

```
<210> SEQ ID NO 19
<211> LENGTH: 19
<212> TYPE: DNA
<213> ORGANISM: Artificial Sequence
<220> FEATURE:
<223> OTHER INFORMATION: Primer for qPCR

<400> SEQUENCE: 19
gctgggcatc aaggtcaag                                                  19

<210> SEQ ID NO 20
<211> LENGTH: 20
<212> TYPE: DNA
<213> ORGANISM: Artificial Sequence
<220> FEATURE:
<223> OTHER INFORMATION: Primer for qPCR

<400> SEQUENCE: 20
atctcatcct tcggctcaac                                                 20
```

DOUBLE-STRANDED RNA-BASED NANOPARTICLES FOR INSECT GENE SILENCING

CROSS-REFERENCE TO RELATED APPLICATIONS

The present application claims the priority benefit of U.S. Provisional Patent Application Ser. No. 61/491,729, filed May 31, 2011, entitled DOUBLE-STRANDED RNA-BASED NANOPARTICLES FOR INSECT GENE SILENCING, incorporated by reference in its entirety herein.

SEQUENCE LISTING

The following application contains a sequence listing in computer readable format (CRF), submitted as a text file in ASCII format entitled "SequenceListing," created on May 8, 2012, as 41 KB. The content of the CRF is hereby incorporated by reference.

BACKGROUND

1. Field of the Invention

The present disclosure relates to RNAi methods of pest management using oral delivery of polymeric/dsRNA nanoparticles to target insects.

2. Description of Related Art

RNA interference (RNAi) is a mechanism using double-stranded RNA (dsRNA) or small interfering RNA (siRNA) to trigger post-transcriptional gene silencing that destroys mRNA of a particular gene to prevent translation and the formation of an active gene product (most commonly a protein). The discovery of RNAi has not only provided a breakthrough in the methodology for functional analysis of genes, but also opened a novel avenue for treating human diseases and protecting crops against insect pest damages.

Although RNAi is a conserved mechanism in eukaryotes including fungi, plants, insects and mammals, there have been great challenges for successful RNAi in some organisms or some stages of an organism. Such difficulties may be attributed to the lack of effective delivery methods for dsRNA or siRNA, and the instability of these nucleic acids during and/or after the delivery. Currently, direct injection of dsRNA is the most commonly used delivery method for RNAi. However, injection has many drawbacks including: 1) it can be technically demanding and time consuming, 2) limitations exist in certain insect species (e.g., small size and aquatic living); 3) often lack of effectiveness in triggering RNAi, probably due to the absence of or inadequate cellular uptake of dsRNA in the larval tissues; and 4) limitations in the ability to inject a sufficient number of insects.

The success of RNAi is also largely determined by the stability of dsRNA or siRNA during and/or after the delivery. It has been reported that half-life for naked siRNA in serum ranges from several minutes to about an hour. Such a short half-life of the nucleic acids will not lead to an adequate RNAi response in an organism unless a high dose of dsRNA or siRNA is applied. To increase the stability of dsRNA or siRNA and enhance their cellular uptake, polymeric nanoparticles have been used for nucleic acid delivery in RNAi-based gene therapeutics.

There has been great interest and effort in mosquito research due to the significant impact mosquitoes have on human health and well-being in the world. In mosquitoes, RNAi is usually performed by injection of dsRNA during the adult stage. RNAi in mosquito larvae has not been well established due to their aquatic habitat and unavailability of effective dsRNA delivery systems for the larvae. Therefore, improved delivery methods for RNAi in mosquitoes and other insects are greatly needed.

SUMMARY

The present disclosure is broadly concerned with a nanoparticle useful for RNAi of a target insect gene. The nanoparticle comprises a polymer matrix and insect dsRNA. In one or more embodiments, the insect dsRNA comprises a first strand and a second strand, wherein at least one strand comprises a region of complementarity that is substantially complementary to at least a portion of an mRNA transcript of the target insect gene or to at least a portion of an mRNA encoding a protein of the target insect gene.

A method of silencing a target gene in a target insect using RNAi is also provided. The method comprises providing an effective amount of a nanoparticle comprising a polymer matrix and dsRNA, and placing the nanoparticle in a location where insects may come into direct contact therewith. The nanoparticles are orally ingested by the target insect, and the ingested nanoparticles trigger gene silencing of the target gene in the target insect. In one or more embodiments, the dsRNA of the ingested nanoparticles is cleaved into siRNAs in the target insect, which triggers the gene silencing.

An insect bait useful for oral administration of dsRNA for RNAi in insects is also provided. The bait comprises a nanoparticle and an edible insect attractant dispersed or dissolved in a carrier. The nanoparticle comprises a polymer matrix and insect dsRNA. In one or more embodiments, the insect baits are environmentally-friendly and/or biodegradeable.

Modified insects are also provided, which have been modified using oral RNAi methods. The insects have increased susceptibility to a pesticide. In one or more embodiments the modified insects have decreased chitin content, disruption of the peritrophic matrix, or a combination thereof. In related embodiments, the modified insects have decreased levels of mRNA transcripts of a chitin synthase gene or decreased levels of chitin synthase.

A method of screening of a target gene function in an insect is also provided. The method comprises providing an effective amount of a nanoparticle, placing the nanoparticles in a location for feeding the nanoparticles to the insect, wherein the nanoparticles are orally ingested by the insect, and analyzing changes in the insect to evaluate the function of the target gene. The nanoparticles comprise a polymer matrix and insect dsRNA. The dsRNA comprises at least one strand having a region of complementarity that is substantially complementary to at least a portion of an mRNA transcript of the target gene.

BRIEF DESCRIPTION OF THE DRAWINGS

FIG. 1 is a Table listing primers used in the working example, which are also listed in the Sequence Listing;

DETAILED DESCRIPTION

Figure 2:
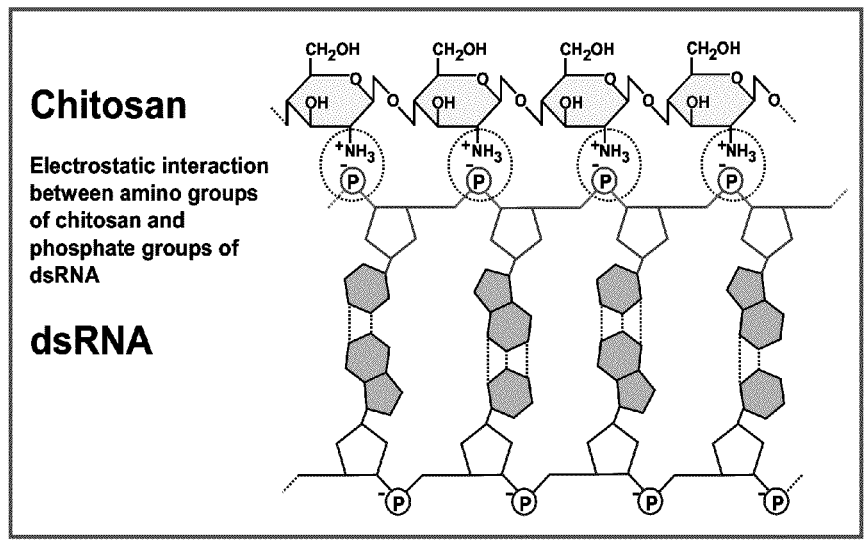
FIG. 2 is a Schematic representation of electrostatic interactions between chitosan and dsRNA in the nanoparticles.

The disclosed embodiments are concerned with a novel and effective oral delivery RNAi method for insects. Unless otherwise specified, the term "insect" is used herein to refer to both larval—as well as adult-stage insects. The embodiments are suitable for use with various insect pests, including (without limitation) mosquitoes, beetles, caterpillars, cockroaches, locusts, termites, and the like. In general, the method utilizes novel nanoparticles assembled from a polymeric material and the dsRNA of interest, which can be ingested by the target pest. Because feeding is not restricted by insect size and developmental stage, the oral delivery method also holds a great potential for high throughput screening of various genes for their functions, as discussed in more detail below.

In one or more embodiments, novel nanoparticles for insect RNAi are provided. The nanoparticles comprise a polymer matrix and dsRNA, wherein the dsRNA is retained by the polymer to thereby form the nanoparticle structure. In one or more embodiments, the dsRNA is coupled or bound to the polymer, for example, via electrostatic or ionic interaction, covalent bonding, or Van der Waals forces. In some embodiments, the dsRNA can be physically entrapped in the polymeric matrix, but not necessarily coupled or bonded thereto. In some embodiments, the dsRNA is coupled to the polymer, but is not covalently bound thereto (i.e., relies on some other attractive force). As used herein, the term "nanoparticle" refers to nanosized particles or nanoparticulate structures with at least one dimension (maximum surface-to-surface measurement) of less than about 200 nm. For example, in the case of spherical-shaped nanoparticles, the diameter will be less than about 200 nm. Unless otherwise noted, the term "dsRNA" is used herein to encompass both dsRNA and siRNA.

Polymers for use in preparing the nanoparticles include biopolymers, although certain synthetic polymers may also be used. The term "biopolymer" is used herein to encompass polymers derived from natural materials and/or living organisms. The polymers are preferably biodegradable, biocompatible, and/or substantially non-toxic. Exemplary polymers will be cationic to facilitate electrostatic interaction and coupling with the negatively-charged dsRNA. Suitable polymers are also preferably water soluble. Biopolymers include cellulose, chitin, starch, collagen, and derivatives thereof, such as chitosan which is a deacetylated chitin polymer. A particularly preferred polymer for use in preparing the dsRNA nanoparticles is chitosan. Chitosan is a widely-available, virtually non-toxic, and biodegradable polycationic polymer that can be prepared by deacetylation of chitin. Suitable dsRNA for use in the inventive nanoparticles can be prepared based upon all or a portion of any target gene sequence or corresponding cDNA of a target insect species to be modified via gene silencing according to one or more embodiments. In other words, the dsRNA used in the invention is specific to the target insects. The dsRNA is preferably from about 200 to about 1,000 base pairs (bp) in length, more preferably from about 300 to about 600 bp in length, and even more preferably from about 400 bp to about 500 bp in length. The dsRNA will comprise a first (sense) strand and a second (antisense) strand. In one or more embodiments, at least one strand (i.e., the antisense strand) will be substantially complementary to at least a portion of an mRNA transcript of a target gene or an mRNA encoding a target gene product (protein). In other words, at least one strand of the dsRNA will have a region of complementarity that is substantially complementary to at least a portion of an mRNA of the target gene for the dsRNA molecule to direct cleavage of the RNA via RNAi. In some embodiments, the antisense strand includes a region of complementarity of at least about 21 (and preferably at least about 23) nucleotides in length. In one or more embodiments, the antisense strand includes a region of complementarity having full complementarity with an mRNA of the target gene.

Those skilled in the art will appreciate that dsRNA can be synthesized using primers designed from the target gene cDNA sequences and commercially-available transcription kits. For example, in one or more embodiments, mRNA of a target insect species can be extracted and used to synthesize cDNA of which all or a portion is used as a template to transcribe dsRNA. Known cDNAs can also be used to synthesize the dsRNA without having to extract mRNA from the target species. Regardless of how it is synthesized, when introduced into the pest, the dsRNA is cleaved into siRNAs approximately 20-25 bps in length, triggering RNAi and silencing the endogenous target gene. Gene silencing can occur by partially, substantially, or completely inhibiting, repressing, or suppressing the expression, activity, and/or function of the target gene or gene product.

In one or more embodiments, the target gene is an insect chitin synthase gene, such as CHS1 and/or CHS2. The cDNA sequences and deduced amino acid sequences for CHS1 and CHS2 in *Anopheles gambiae* (African malaria mosquito) are shown in SEQ ID NO:1 through SEQ ID NO: 4. In one or more embodiments, the dsRNA comprises a first strand (e.g., sense strand) and a second strand (e.g., antisense strand), wherein at least one strand (e.g., the antisense strand) comprises a region of complementarity that is substantially complementary to at least a portion of an mRNA transcript of a chitin synthase gene. In related embodiments, the dsRNA comprises a first strand (e.g., sense strand) and a second strand (e.g., antisense strand), wherein at least one strand (e.g., the antisense strand) comprises a region of complementarity that is substantially complementary to at least a portion of mRNA encoding chitin synthase. In one or more embodiments, at least one strand of the dsRNA is a transcript of SEQ ID NO: 1 or SEQ ID NO: 3, or any portion thereof, and preferably a contiguous portion thereof of at least about 200 nucleotides. In related embodiments, at least one strand of the dsRNA is selected from the group consisting of: a transcript of residues 2,267 to 2,635 of SEQ ID NO: 1, a transcript of residues 3,812 to 4,202 of SEQ ID NO: 1, a transcript of residues 3,846 to 4,235 of SEQ ID NO:3, and a transcript of residues 3,331 to 3719 of SEQ ID NO: 3.

The nanoparticles can be prepared by mixing the selected polymer and dsRNA in a solvent system. More specifically, a polymer solution can be prepared by dispersing or dissolving the selected polymer in a solvent system. Suitable polymer solvent systems will depend upon the polymer(s) used. In one or more embodiments, an exemplary solvent system comprises sodium acetate and acetic acid, and more preferably, 0.1 M sodium acetate and 0.1 M acetic acid at pH 4.5. The dsRNA is also dispersed in a solvent system. Suitable dsRNA solvent systems will typically include a solvent such as sodium sulfate, and preferably 50 mM sodium sulfate. The polymer and dsRNA solutions are then mixed together, followed by heating to a temperature of from about 50 to about 60° C. (preferably about 55° C.) for a time period of from about 30 to about 90 seconds (preferably about 60 seconds). The mixture is then vortexed for a time period of from about 30 to about 90 seconds (preferably about 60 seconds). Advantageously, the polymer and dsRNA will self-assemble into the nanoparticles, preferably via electrostatic interaction between the dsRNA and polymer matrix. In one or more embodiments, the dsRNA and polymer are bound together via electrostatic attraction forces. In some embodiments, the dsRNA and polymer are not covalently bound to one another. In related embodiments, the dsRNA becomes substantially entrapped (physically or chemically) by the polymer matrix. The N:P charge ratio, which is defined as the ratio of chitosan amino groups (N) to dsRNA phosphate groups (P), is preferably from about 1:1 to about 10:1, and more preferably from about 3:1 to about 5:1. The dsRNA is preferably stabilized by the polymer matrix. In particular, when subjected to a dsRNA Retention Test, as described herein, greater than about 90% of the dsRNA will be retained in the nanoparticles (in other words, less than about 10% dsRNA will be released by the nanoparticles). In one or more embodiments, the resulting polymeric/dsRNA nanoparticles are substantially spherical or ellipsoidal in shape, with an average diameter of less than about 200 nm, preferably from about 100 nm to about 200 nm. Although the initial polymer is preferably water-soluble, as noted above, in one or more embodiments, the nanoparticles are water-insoluble, but preferably remain biodegradeable and non-toxic to the environment.

The efficiency of RNAi can be improved by modifying the surface of the nanoparticles to enhance its uptake by insect cells. For example, polyethylenimine (PEI) can be used to modify the surface of chitosan/dsRNA nanoparticles to enhance the uptake of the nanoparticles by insect cells.

The nanoparticles can be incorporated into an insect bait suitable for oral administration of the nanoparticles to the target insect. The bait composition comprises the polymeric/dsRNA nanoparticles dispersed in a carrier, along with an edible insect attractant. Typically, the nanoparticles and attractant are mixed together before being dispersed in the desired carrier. Suitable attractants would be any type of insect food and/or attractant which will lure the insect to the bait to ingest the bait composition (including the nanoparticles). Exemplary insect foods or attractants include any type of insect food, including various sugars, proteins, carbohydrates, yeast, fats, and/or oils. It will be appreciated that the bait could be in any form suitable for delivery and ingestion of the nanoparticles (and thus may depend upon the habitat and target insect), but will typically be a liquid, gel, or self-sustaining gel-matrix, although solid baits (e.g., tablets, granules, etc.) are also contemplated. Exemplary carriers include, without limitation, agarose gel, gelatin gel, and/or pectin gel. In one or more embodiments, the carrier is agarose gel, which is especially suited for aquatic habitats and breeding grounds. The polymeric/dsRNA nanoparticles are present in the bait composition in an effective amount (i.e., concentration) for gene silencing. The concentration of nanoparticles in the bait is preferably from about 0.1 to about 5% by weight, and more preferably from about 0.15 to about 2% by weight, based upon the total weigh of the bait taken as 100% by weight. The weight ratio of nanoparticles to insect attractant (food) in the bait is preferably from about 1:20 to about 1:200, and more preferably from about 1:50 to about 1:100.

The method embodiments are directed towards novel oral dsRNA delivery methods for RNAi in insects. The methods can also be used to increase the pesticide susceptibility of an insect. The invention is especially suited for targeting insects with aquatic habitats or breeding grounds, or for formulating baits for control of even non-aquatic insect pests. Exemplary insects that could be targeted using the inventive methods include mosquitoes, beetles, caterpillars, cockroaches, locusts, termites, and the like. The method comprises feeding an effective amount of the polymeric/dsRNA nanoparticles to the target insects, or providing an effective amount of polymeric/dsRNA nanoparticles in a location where insects may come into direct contact therewith, and the nanoparticles are then fed upon or ingested by insects, including the target insects. The process can be repeated by repeating the process and adding additional polymeric/dsRNA nanoparticles and/or replacing or refreshing the insect bait as necessary (e.g., every 24-48 hours). In one or more embodiments, the insects feed upon the bait (including the nanoparticles) for at least about 3 days, preferably from about 3 to about 5 days, and more preferably from about 4 to about 5 days. The insects can be treated with a pesticide concurrently with, or after ingestion of the nanoparticles. In one or more embodiments, a pesticide is delivered into the location where the insects have been feeding on the bait. In one or more embodiments, the pesticide can be applied or delivered about 4 days (day 4) after the initial day (day 1) of ingestion of the nanoparticles. As explained above, ingestion of the polymeric/dsRNA nanoparticle by the insect triggers post-transcriptional gene silencing of the target gene.

The method can be used to interfere with the growth and development of the insect, including completely silencing the target gene leading to mortality, or otherwise partially or completely silencing the expression, activity, or function of the target gene leading to increased susceptibility of the target insect to pesticides. In particular, the reduction in transcript levels from gene silencing results in lowered levels of the target protein, resulting in phenotypic changes in the modified insect. In the case of chitin synthase genes, gene silencing can lead to decreased chitin content as well as disruption of the peritrophic matrix in the target insect, resulting in mortality and/or increased susceptibility to a pesticide, such as calcofluor white, dithiothreitol, and/or diflubenzuron. In one or more embodiments, susceptibility to an insecticide can be increased by 25% or more as compared to the susceptibility of non-modified or control insects.

A further embodiment of the invention is concerned with affected or modified insects having inhibited, repressed, or suppressed expression, activity, or function of the target gene, mRNA transcripts, or expressed protein, wherein the modified insects have increased susceptibility to pesticides. In one or more embodiments, the modified insects have inhibited, repressed, or suppressed expression, activity, or function of a chitin synthase gene, or other genes that control insect activity, behavior, reproduction, growth and/or development. In one or more embodiments, the modified insect has decreased levels of an mRNA transcript of a chitin synthase gene. In related embodiments, the modified insect has decreased levels of chitin synthase. In one or more embodiments, the modified insect has decreased levels of a protein having SEQ ID NO:2 or 4, or a protein having at least about 80% sequence identity (preferably about 90% sequence identity) to SEQ ID NO: 2 or 4, and retaining the functional characteristics thereof (i.e., produces chitin).

The present invention has the distinct advantage of being an organism-specific method of pest control. Because the dsRNA which is used to develop the nanoparticles and insect bait can be designed based on specific gene sequences of a target pest species, the baits are safe to other organisms. In addition, since environmentally-friendly polymers are preferred, the preferred nanoparticles and insect baits will also be safe for the environment. In one or more embodiments the baits are environmentally-friendly, which means they are substantially free of hazardous chemicals and/or chemical pollutants and/or are biodegradeable. Moreover, since the susceptibility of the modified insect to pesticides has been increased, less of these chemicals need to be used to treat and control the pests, which further augments the environmental benefits of the present invention.

A further embodiment of the present disclosure is concerned with methods of high-throughput screening of a target gene's functions. The methods comprise providing an effective amount of a polymeric/dsRNA nanoparticle for ingestion by an insect (as described above), and analyzing the effect (e.g., morphologic and/or phenotypic changes) on the insect to thereby determine the function of the target gene.

Additional advantages of the various embodiments of the present disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by those in the art. This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. Where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. The terms "complementary," "fully complementary," and "substantially complementary" herein may be used with respect to the base matching between the sense strand and the antisense strand of a dsRNA, or between the antisense strand of a dsRNA and a target sequence, as will be understood from the context of their use. It will also be understood that where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus. Most preferably, the mismatches are located within 6, 5, 4, 3, or 2 nucleotides of the 5' terminus of the antisense strand and/or the 3' terminus of the sense strand.

Term "control" when used with respect to control insects includes wild-type insects, as well as genetically altered insects that otherwise contain a wild-type, non-modified, or native (endogenous) gene targeted for gene silencing according to the embodiments described herein. A "wild-type" gene is one that has the characteristics of a gene isolated from a naturally occurring source. A "wild-type" gene product is one that has the characteristics of a gene product isolated from a naturally occurring source, whereas "modified" genes or gene products are those having modifications in sequence and/or functional properties (i.e., altered characteristics) when compared to the wild-type gene or gene product. Likewise, "modified" insects are those that have been altered to change the expression, activity, or function of the target genes or gene products, as opposed to non-modified insects.

The term gene "expression" refers to the process of converting genetic information encoded in a gene into RNA (e.g., mRNA, rRNA, tRNA, or snRNA) through transcription of the gene (i.e., via the enzymatic action of an RNA polymerase), and into protein, through translation of mRNA. Gene expression can be regulated at many stages in the process.

The term "pesticide" is used herein to encompass any substance used for destroying/killing insects or other like organisms. The term is used interchangeably herein with "insecticides," "larvacides," and the like, unless otherwise expressly noted.

The "inhibition," "silencing," or "knock down" of the expression, activity, or function of a gene, as used herein, is intended to refer to any suitable method of reducing or even completely suppressing protein expression from a gene or a coding sequence, including methods of reducing mRNA transcripts, as well as the levels of protein produced as a result of gene transcription to mRNA and subsequent translation of the mRNA. Gene inhibition may be effective against a native insect gene associated with a trait, e.g., to provide the insect with a diminished level of a protein encoded by the native gene or with reduced levels of an affected metabolite.

The term "self-sustaining" means that the structure retains a particular shape once that shape is formed, without an external support structure, and is not susceptible to deformation merely due to its own internal forces. The definition includes solids, gels, and pastes.

The term "sequence identity" is used herein to describe the sequence relationships between two or more nucleic acid or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. It will be appreciated that a sequence having a certain % of sequence identity to a reference sequence does not necessarily have to have the same total number of nucleotides or amino acids. Thus, a sequence having a certain level of "identity" includes sequences that correspond to only a portion (i.e., 5' non-coding regions, 3' non-coding regions, coding regions, etc.) of the reference sequence.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

In this Example, we established a novel nanoparticle-based method for RNAi through larval feeding. We then examined the RNAi-mediated repressions of the transcripts for two related genes encoding chitin synthase 1 (AgCHS1) and chitin synthase 2 (AgCHS2). AgCHS1 (also known as AgCHS-A) is responsible for biosynthesis of the chitin found in the cuticular exoskeleton and other tissues that are ectodermal in origin, such as foregut, hindgut and trachea, and is exclusively expressed in epidermal cells and other ectodermal tissues, whereas AgCHS2 (also known as AgCHS-B) is responsible for biosynthesis of the chitin associated with peritrophic matrix (PM) and is specifically expressed in epithelial cells of the midgut. We further examined the effect of the RNAi on the biosynthesis of chitin and larval responses to different chemicals after RNAi, and demonstrated for the first time that the RNAi in mosquito larvae is systemic, a phenomenon in which local administration of dsRNA (e.g., in the gut through feeding) leads to an RNAi response in the whole body through the amplification and spread of silencing to other cells in the body. The results demonstrate the effectiveness of these nanoparticles, and the larval feeding-based method in chitin synthase genes of the African malaria mosquito, however, the invention can find application with other genes of interest and with other insects.

A. Experimental Procedures

1. Mosquito Rearing

A colony of *An. gambiae* initially obtained from the Malaria Research and Reference Reagent Resource Center (MR4) (Manassas, Va.) was maintained in the Department of Entomology at Kansas State University (Manhattan, Kans.) based on the method of Benedict (1997, *Care and maintenance of anopheline mosquito colonies*, in The Molecular Biology of Insect Disease Vectors) with little modifications. Larvae were fed with slurries of brewer's yeast and TetraMin Baby-E fish food, whereas adults were fed with 10% sucrose solution soaked into cotton balls. To allow for the females to lay eggs, the two-day-old females were fed with a membrane feeder made of a lubricated Naturalamb brand condom (Church and Dwight Co., Inc., Princeton, N.J.) containing pre-warmed, defibrinated horse blood. The defibrinated horse blood was purchased from Colorado Serum Company (Denver, Colo.).

2. Preparation of Chitosan/dsRNA Nanoparticles

To prepare dsRNA for each CHS gene, specific primers were designed based on the annotated AgCHS1 (GenBank accession no. XM_321337, SEQ ID NO: 1) and AgCHS2 (GenBank accession no. AY056833, SEQ ID NO: 3) cDNA sequences. After total RNA was extracted from mosquito larvae with TRIzol reagent (Invitrogen, Carlsbad, Calif.), 3.5 µg of total RNA was used to synthesize the first strand cDNA using the First Strand cDNA Synthesis kit (Fermentas, Glen Burnie, Md.). To prepare GFP dsRNA for negative RNAi controls, specific primers were designed and a 684-bp fragment was amplified using the plasmid 11335: GFP::L4440 (Addgene Inc., Cambrige, Mass.) as a template. The sequences of the primers used for dsRNA synthesis are shown in Table I (FIG. 1). Each dsRNA was prepared using a MEGAScript RNA® kit (Ambion, Austin, Tex.) based on the manufacture's procedure.

For generating the chitosan/dsRNA nanoparticles, chitosan from crab shells (catalog no. C3646-25G, ≥75 deacetylated; Sigma-Aldrich, Milwaukee, Wis.) was dissolved in sodium acetate buffer (0.1 M sodium acetate-0.1 M acetic acid, pH 4.5) to make a 0.02% wt/vol working solution. A total of 32 µg of dsRNA in 100 µl of 50 mM sodium sulfate was added to 100 µl of chitosan solution. The amounts of dsRNA and chitosan were balanced for their efficient electrostatic interactions between chitosan and dsRNA. After the mixture was heated at 55° C. for 1 min, it was immediately mixed by vortexing for 30 s using a high-speed vortex (Model 232, Fisher Scientific, Pittsburgh, Pa.) to allow the formation (self-assembly) of the nanoparticles.

3. Preparation of Mosquito Larval Food Containing the Chitosan/dsRNA Nanoparticles Once formed, the nanoparticles were first centrifuged at 13,000 g for 10 min followed by mixing the resultant pellet with 6 mg of ground mosquito larval food consisting of TetraFin goldfish flakes (Tetra Holding, Inc., Blacksburg, Va.) and dry yeast (Universal Foods Corp., Milwaukee, Wis.) at a ratio of 2:1. Both the goldfish flakes and yeast were ground to small particles (>300 μm as measured by no. 50 USA standard test sieve). The mixture of the food and the nanoparticles was then coated by thoroughly mixing with 30 μl of 2% pre-melted agarose (genetic analysis grade; Fisher Scientific) gel solution at 55° C. The mixture was then allowed to solidify into a gel. The solidified gel containing both the food and the nanoparticles was cut into small pieces (approximately 1 mm thick) using a razor blade, which were then used to feed mosquito larvae in water.

4. Larval Feeding on Food Containing the Chitosan/dsRNA Nanoparticles

A group of 15-20 3rd-instar mosquito larvae was transferred into a 500-ml glass beaker containing 100 ml of deionized water. One sixth of the gel slices that were prepared from 32 μg of dsRNA, as described above, were added into each beaker. Approximately an equal amount of the gel slices was used to feed the larvae once a day for a total of four days. Any potential phenotypic changes were visually examined in the larvae during the experiment. The transcript levels of AgCHS1 or AgCHS2, chitin contents, and other phenotypic changes were assessed in the larvae at the end of the experiment (i.e., day 4).

5. Atomic Force Microscopy (AFM) Imaging

To confirm the nanoparticle formation between chitosan and dsRNA, AFM was used to examine the nanoparticles using a tapping mode with a high aspect ratio tip. Briefly, 30 μl of the nanoparticle solution was placed onto freshly cleaved mica, washed with deionized water twice, and dried with $N_2$. AFM images on different locations of the mica were then obtained using a Nanoscope IIIa scanning probe microscope (Equipment for Technology & Science Inc., San Jose, Calif.).

6. RT-PCR and qPCR Analysis

Total RNA was extracted from mosquito larvae with TRIzol reagent (Invitrogen, Carlsbad, Calif.) and 3.5 μg of total RNA was used for first strand cDNA synthesis using the First Strand cDNA Synthesis kit (Fermentas, Glen Burnie, Md.). The first strand cDNA was then used as template for PCR and qPCR. A gene encoding ribosomal protein S3, AgRPS3, was used as an internal reference. PCR was performed with a PCR Master Mix kit (Fermentas). The qPCR was performed using a Maxima SYBR Green qPCR Master Mix (Fermentas), and the $2^{-\Delta\Delta C_T}$ method was used to calculate the relative levels of AgCHS1 and AgCHS2 transcripts in the mosquito larvae fed on the food containing the AgCHS1 or AgCHS2 dsRNA-based nanoparticles as compared with the control larvae fed on the food containing the GFP dsRNA-based nanoparticles. The sequences of the primers used for RT-PCR and qPCR analyses are shown in Table I (FIG. 1).

7. Retention of dsRNA by Chitosan/dsRNA Nanoparticles (dsRNA Retention Test)

To determine whether the dsRNA entrapped in the nanoparticles can be effectively retained in the slices of the food gel when added into water, 20 μg of dsRNA entrapped in the polymeric matrix were mixed with food to make food gel as described above. Control food gel was prepared in the same way except that dsRNA was directly mixed with food without using nanoparticles. After the slices of the food gel were incubated in 1 ml water for 24 h, samples were centrifuged at 13,000 g for 10 min, and free dsRNA released from the food gel in the supernatant was extracted by phenol/chloroform. The extractant was then dissolved in 30 μl water, and dsRNA concentration was determined using an Ultrospec 3000 UV/visible spectrophotometer at 260 nm. For visual comparisons of dsRNA retention in the two samples, 4 μl of each extractant was examined on 1.2% agarose gel. The dsRNA bands were visualized using ethidium bromide that was incorporated into the agarose gel and TB running buffer.

8. Chitin Content Assay

Chitin content of the mosquito larvae was assayed based on a technique commonly used to quantify the chitin content of fungal cell wall materials present in infected animal organs and tissues. Briefly, 15 third-instar mosquito larvae were homogenized in 0.5 ml of distilled water using a glass-pestle homogenizer. The pestle and homogenizer were rinsed with 0.5 ml of distilled water which was subsequently combined with the homogenate. The 1.0-ml homogenates were centrifuged at 4,000 g for 15 min at room temperature and the pellet of each sample was resuspended in 0.4 ml of 3% SDS (sodium dodecyl sulfate). The samples were then incubated at 100° C. for 15 min and centrifuged again for 10 min after cooling. After each pellet was washed with 0.5 ml distilled water, it was resuspended in 0.3 ml of 14M KOH. To deacetylate the chitin, the samples were incubated at 130° C. for 1 h followed by cooling them on ice for 5 min. After 0.8 ml of ice-cold 75% ethanol was added to each sample, the sample was mixed and incubated on ice for 15 min. Next, 30 μl of Celite 545 (Fisher Scientific, Pittsburgh, Pa.) suspension was then added to each sample, and the samples were centrifuged at 4,000 g for 5 min at 4° C. After each pellet containing insoluble chitosan (i.e., glucosamine polymer) was washed with 0.5 ml of 40% cold ethanol and 0.5 ml of cold distilled water, the chitosan in each tube was resuspended in 0.5 ml of distilled water.

For the colorimetric chitin content assay, 100 μl of the chitosan solution was mixed with 50 μl of 10% $NaNO_2$ and 50 μl of 10% $KHSO_4$, and gently shaken three times during a 15-min incubation period at room temperature. Mixing these chemicals allowed the generation of $HNO_2$ to depolymerize the chitosan and deaminate the glucosamine residues from the chitosan. After the samples were centrifuged at 4,000 g for 15 min at 4° C., 60 μl of the supernatant of each sample was transferred to a new 1.5-ml microcentrifuge tube followed by the addition of 20 μl of $NH_4SO_3NH_2$. The mixtures were then vigorously shaken for 5 min at room temperature. After 20 μl of freshly prepared MBTH (3-methyl-2-benzothiazolone hydrazone hydrochloride hydrate, Sigma-Aldrich, St. Louis, Mo.) was added to each sample, mixtures were incubated at 100° C. for 5 min in a water bath. The samples were then cooled at room temperature for 25 min, and 100 μl of each sample was transferred to a well of a 96-well microplate. Absorbance was determined at 650 nm in a Vmax microplate reader (Molecular Devices, Menlo Park, Calif.). Chitin content was expressed as a glucosamine equivalent according to a standard curve constructed using known concentrations of glucosamine (Sigma-Aldrich).

9. Chemical Treatment and In Vivo Assay of Peritrophic Matrix (PM) Disruption

After mosquito larvae were fed with the food containing the chitosan/dsRNA nanoparticles for four days, they (15-20 larvae) were transferred to a 500-ml glass beaker containing 100-ml deionized water. Diflubenzuron (DFB) (catalog no. PS-1028; Chem Service, West Chester, Pa.) stock solution in acetone was then added to each beaker to obtain a final DFB concentration of 200 μg/L. The larval mortality was assessed at 24 h. For calcofluor white (CF; Fluorescent Brightener 28, catalog no. F3545-5G; Sigma-Aldrich) and dithiothreitol (DTT; electrophoresis grade; Fisher Scientific) treatments and their subsequent assays of the PM permeability, previously described methods were followed. In brief, each group of untreated larvae (1st control), the GFP-dsRNA-fed larvae (2nd control), and the AgCHS2-dsRNA-fed larvae were transferred into 5 ml of deionized water containing DTT at 2.5 mM, or CF at 3 or 4 mg/ml, and agar (Becton, Dickinson and Company, Sparks, Md.) at 0.3 mg/ml. After the larvae were maintained overnight (17-18 h) at 25° C., larval mortality was recorded and the surviving larvae were rinsed thoroughly with deionized water and transferred to 2 ml of 2% (w/v) blue dextran (molecular weight 2,000,000 Da, catalog no. D5751-5G; Sigma-Aldrich) for 1 hr. The dye in the gut was examined under a Leica M205 FA stereomicroscope. Images were captured using a Leica DFC 400 digital camera (Vasha Scientific Inc., Norcross, Ga.) attached to the microscope. The blue gastric caecae (GC) following ingestion of blue dextran indicates a disruption of larval PM.

10. Statistical Analysis

For data obtained from qPCR, relative expression levels in percentage were calculated by dividing the relative expression value (REV) of each gene in the AgCHS dsRNA-treated larvae by the REV of the same gene in the GFP dsRNA-treated larvae. After the percentage data of the relative AgCHS expression were transformed using arcsine square root transformation, the transformed data were subjected to ANOVA followed by Fisher's least significant difference (LSD) multiple comparisons to separate the means among the treatments using ProStat software (Poly Software International, Pearl River, N.Y.).

B. Results

1. Generation of Nanoparticles for Mosquito RNAi Through Larval Feeding

Figure 3:
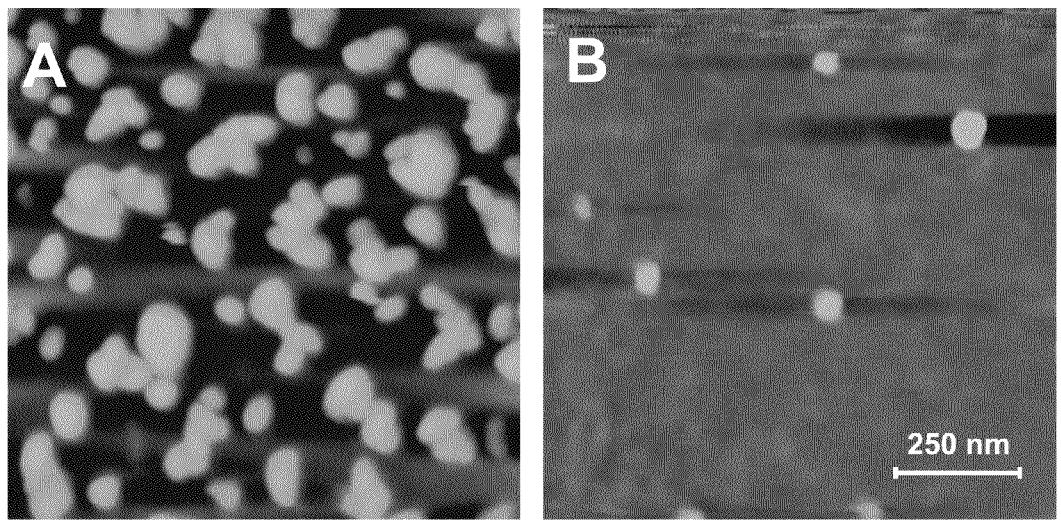
FIG. 3(A) is an atomic force microscopy (AFM) image of the chitosan/dsRNA nanoparticles from the working example.
FIG. 3(B) is an AFM image of the chitosan solution without the addition of dsRNA.

The chitosan/dsRNA nanoparticles were formed by self-assembly of polycations with dsRNA through the electrostatic forces between positive charges of the amino group in the chitosan and negative charges carried by the phosphate group on the backbone of the dsRNA (FIG. 2). The atomic force microscopy (AFM) images of the chitosan/dsRNA nanoparticles showed spherical- or ellipsoidal-shaped structures of similar sizes with diameters ranging from 100 to 200 nm (FIG. 3(A)). In contrast, the control samples in the absence of dsRNA did not form a significant number of nanoparticles. Instead, we found only few smaller and spherical-shaped particles with an average diameter of 70 nm (FIG. 3(B)). All of the scan sizes of the images in FIGS. 3(A)-(B) were 1.0 μm×1.0 μm.

2. dsRNA Retention Test

Figure 4:
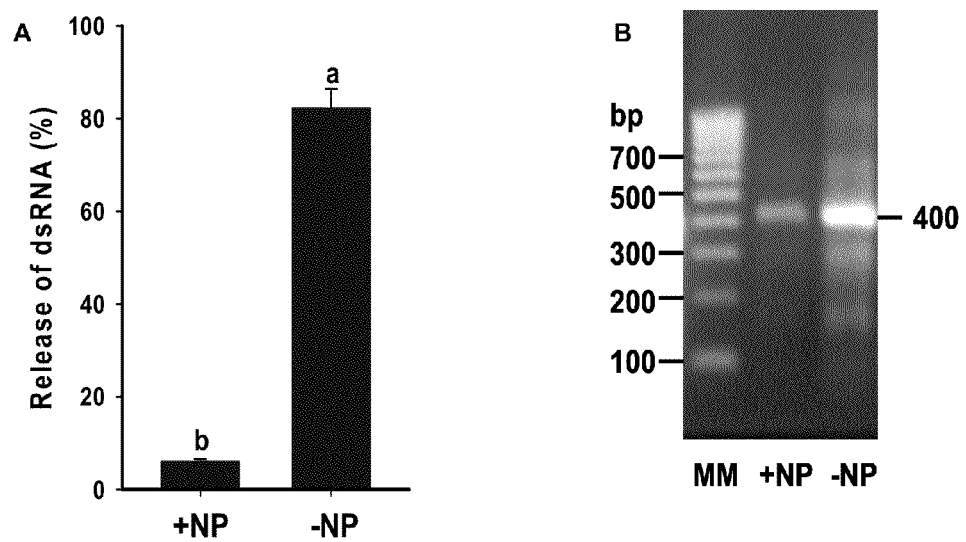
FIG. 4(A) is a graph showing retention of dsRNA by the chitosan/dsRNA nanoparticles in the food gel. +NP: dsRNA entrapped in the nanoparticles; −NP: dsRNA used directly without the nanoparticles. The data are presented as means±SEM of triplicate samples.
FIG. 4(B) is an image of the retention of dsRNA by the chitosan/dsRNA nanoparticles in the food gel as evaluated by agarose gel electrophoresis.

After the insect bait with nanoparticles were incubated in water for 24 h, only about 6% by weight of dsRNA was released from the gel slices into water (FIGS. 4(A), (B)). In contrast, >80% by weight of dsRNA in the gel slices was released into water when dsRNA was directly mixed in the food gel without nanoparticles. These results indicated that our chitosan/dsRNA nanoparticles can effectively protect dsRNA from being released into water from the sliced food gel and can perhaps stabilize dsRNA that is incorporated into the chitosan/dsRNA complex.

3. RNAi for Two Chitin Synthase Genes in Mosquito Larvae

Figure 5:
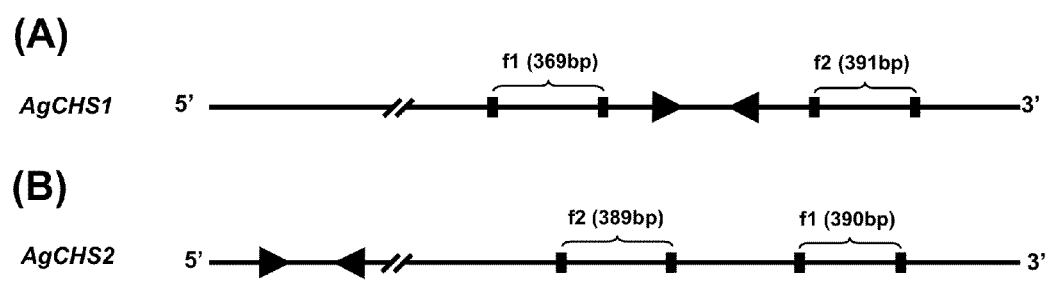
FIG. 5(A)-(B) are diagrams illustrating the regions for designing two dsRNA fragments (i.e., f1 and f2) from each of the two genes (AgCHS1 and AgCHS2). Arrow heads indicate the primer regions for examining the transcript level of each gene by qPCR.

To evaluate the effectiveness of our nanoparticle-based RNAi method in silencing both AgCHS1 and AgCHS2 genes through mosquito larval feeding, two dsRNAs (i.e., dsAgCHS1-f1 and f2 or dsAgCHS2-f1 and f2) were in vitro synthesized for each gene and used to generate chitosan/dsRNA nanoparticles. AgCHS1-f1 was synthesized using residues 2,267 to 2,635 of SEQ ID NO: 1 as the template. AgCHS1-f2 was synthesized using residues 3,812 to 4,202 of SEQ ID NO: 1 as the template. AgCHS2-f1 was synthesized using residues 3,846 to 4,235 of SEQ ID NO: 3 as the template. AgCHS2-f2 was synthesized using residues 3,331 to 3,719 of SEQ ID NO: 3 as the template. One primer pair without overlapping with the dsRNA regions was synthesized for examining the repression of gene transcript by quantitative real-time PCR (qPCR) (FIGS. 5A, B).

Our results clearly showed that feeding 3rd-instar mosquito larvae with either dsAgCHS1- or dsAgCHS2-based nanoparticles effectively triggered RNAi in the larvae. Specifically, dsAgCHS1-f1 and dsAgCHS1-f2 (both from AgCHS1) repressed the transcript levels of AgCHS1 by 62.8 and 52.4%, and AgCHS2 by 48.4 and 57.9%, respectively (FIG. 6(A)). Thus, feeding the larvae with dsRNA of AgCHS1 not only repressed AgCHS1 expression but also AgCHS2 expression. Comparison of the cDNA sequences between AgCHS1-f1 and AgCHS2 using a sequence alignment technique showed a sequence identity of 70.4%. Comparison of the sequences between AgCHS1-f2 and AgCHS2 showed a sequence identity of 54.8%.

Figure 6:
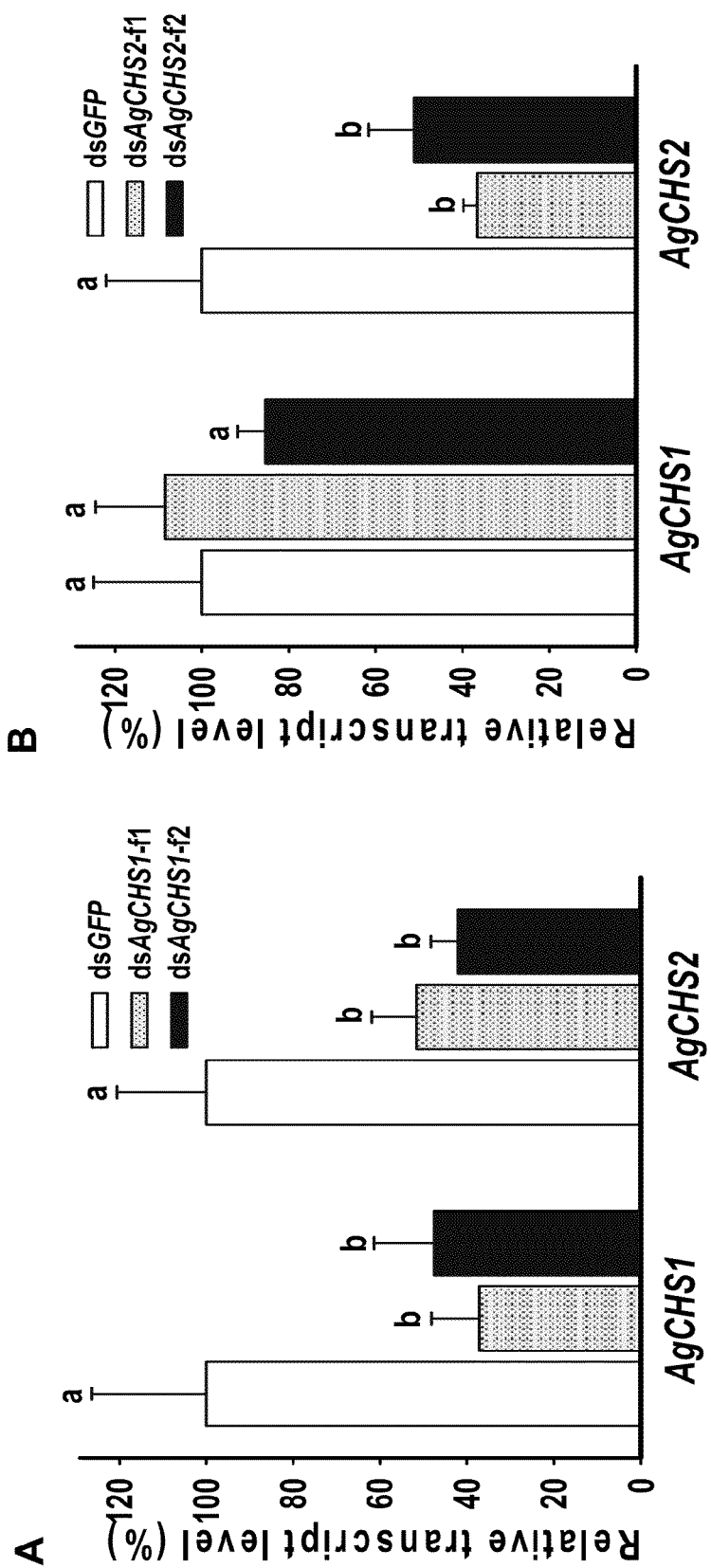
FIG. 6(A) is a graph of the relative transcript levels of AgCHS1 and AgCHS2 in the larvae continuously fed for 4 days (once a day) on each of the two AgCHS1 dsRNA fragments or GFP dsRNA (as controls) that were incorporated into the nanoparticles. The data are presented as means±SEM of five replicate samples.
FIG. 6(B) is a graph of the relative transcript levels of AgCHS1 and AgCHS2 in the larvae continuously fed for 4 days (once a day) on each of the two AgCHS2 dsRNA fragments or GFP dsRNA that were incorporated into the nanoparticles. The data are presented as means±SEM of three replicate samples.

In contrast, dsAgCHS2-f1 and dsAgCHS2-f2 (both from AgCHS2) specifically repressed the transcript levels of AgCHS2 by 63.4 and 48.8%, respectively, but none of these AgCHS2 dsRNAs repressed the transcript level of AgCHS1 (FIG. 6(B)). In FIG. 6, the same letters on the error bars indicate no significant difference based on Fisher's LSD ($P>0.05$). Because AgCHS1 and AgCHS2 also display comparably high cDNA sequence similarities both in dsAgCHS2-f1 and dsAgCHS2-f2 regions (63.7% identity between AgCHS2-f1 and AgCHS1, and 53.8% identity between AgCHS2-f2 and AgCHS1), the non-cross repression was likely due to RNAi triggered by one or more short, but less conserved, sequences in their respective dsRNA.

To examine whether chitosan alone can affect AgCHS gene expression, a separate experiment in which the chitosan/dsRNA nanoparticles were replaced by an equivalent amount of chitosan (0.02 mg in 100 μl) showed no differences in the expression of each gene as compared with the controls in which no chitosan was included in the food. These results indicated no effect of chitosan itself on the AgCHS gene expression in our studies.

Figure 7:
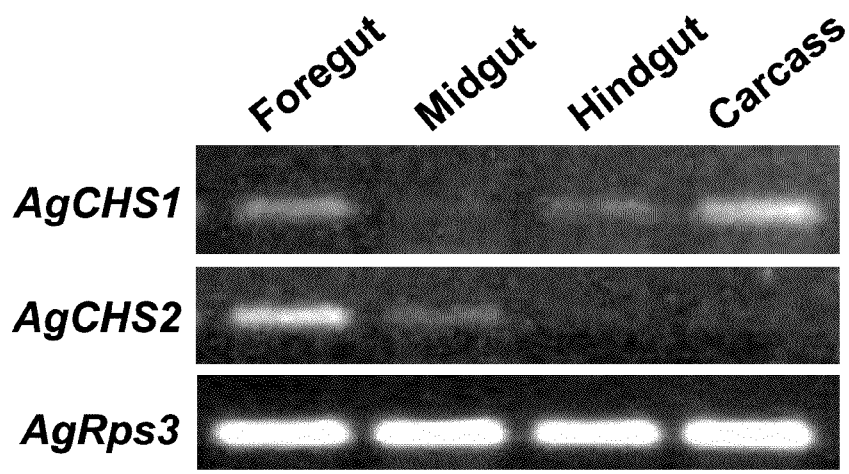
FIG. 7 is an image of the tissue-specific expression patterns of AgCHS as analyzed by RT-PCR in mosquito larvae. Ribosomal protein S3 gene (AgRps3) was used as an internal reference.

We further examined tissue-specific expression profiles of two chitin synthase genes by RT-PCR. As expected, AgCHS1 was most abundantly expressed in larval carcass (i.e., the insect body after its digestive canal is removed) followed by the foregut and hindgut (FIG. 7). However, the expression of AgCHS1 was not detected in the midgut. In contrast, AgCHS2 was most abundantly expressed in the foregut followed by the midgut. However, the expression of AgCHS2 was not detected in the hindgut and carcass (FIG. 7). The high expression of AgCHS2 in the foregut as detected by RT-PCR was most likely due to the fact that it is difficult to separate the cardia, a part of larval midgut, from the foregut during our dissection because the larval foregut is very small and is tightly connected to the cardia of the midgut. Thus, the high expression of AgCHS2 detected in larval foregut might be due to such an artifact in our study.

Figure 8:
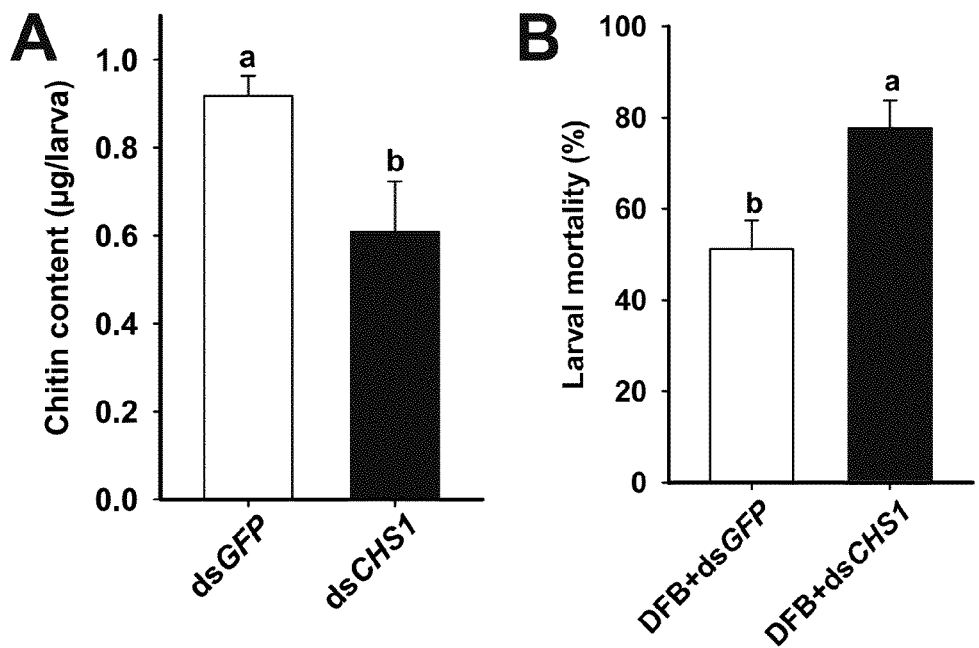
FIG. 8(A) is a graph of the effect of the RNAi on chitin content. The data are presented as means±SEM of four replications (n=4)
FIG. 8(B) is a graph of the effect of the RNAi on susceptibility of the larvae to diflubenzuron (DFB). The data are presented as means±SEM of three replications (n=3)
Figure 9:
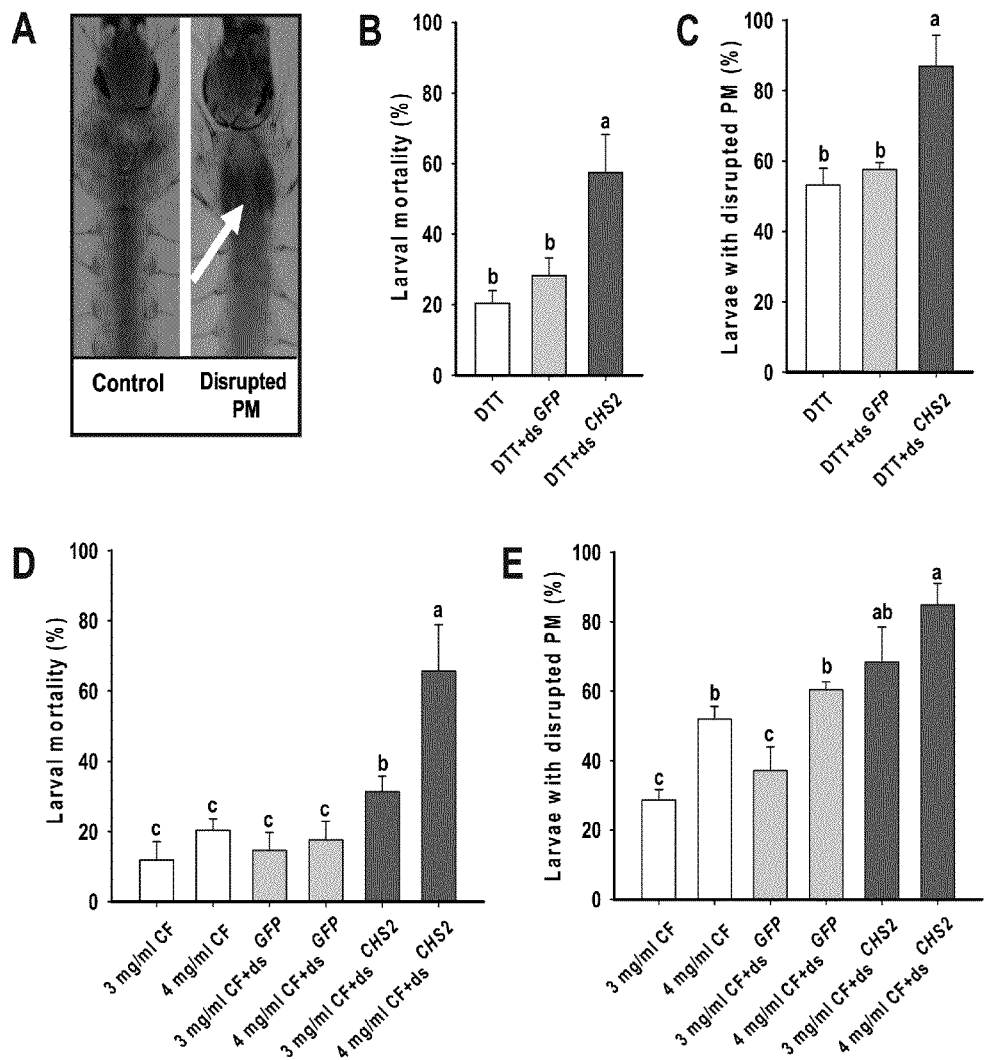
FIG. 9(A) is an image showing the disruption of larval peritrophic matrix by displaying blue gastric caecae (GC) following ingestion of blue dextran. The arrow shows the GC filling with the dye when the PM was disrupted by treating mosquito larvae with dithiothreitol (DTT) or calcofluor white (CF)
FIG. 9(B) is a graph of the effect of the RNAi on larval susceptibility to DTT.
FIG. 9(C) is a graph of the percentages of the surviving larvae with disrupted PM from the same treatments as in (B)
FIG. 9(D) is a graph of the effect of the RNAi on larval susceptibility to CF.
FIG. 9(E) is a graph of the percentages of the surviving larvae with disrupted PM from the same treatments as in (D).

4. Effect of RNAi for AgCHS1 on Chitin Content and Larval Susceptibility to Diflubenzuron After 3rd-instar mosquito larvae were fed on the chitosan/dsRNA nanoparticles, we evaluated the chitin content in the larvae. The RNAi oral delivery method reduced larval chitin content by 33.8% (FIG. 8(A)). Although such a reduction did not lead to larval mortality, the reduction of chitin content significantly increased the susceptibility of the larvae to diflubenzuron (FIG. 8(B)). In FIGS. 8(A)-(B), different letters on the error bars indicate significant difference based on Fisher's LSD ($P<0.05$). Specifically, the mortality of the larvae fed on AgCHS1 dsRNA increased by 26.5% as compared with that of the larvae fed on GFP dsRNA when the larvae were exposed to diflubenzuron at 200 μg/L. The increased mortality in the AgCHS1 dsRNA-fed larvae was caused by reduced chitin content in larval cuticle due to the RNAi of AgCHS1.

5. Effect of RNAi for AgCHS2 on Larval Susceptibility and PM Permeability to Dithiothreitol and Calcofluor White We further investigated the effect of RNAi of AgCHS2 on the survivorship of mosquito larvae and the permeability of their PM. The disruption of the PM by dithiothreitol or other reagents was expected to result in the increase of the PM permeability which can be visualized by distinct blue color in the gastric caecae when insects were fed on blue dextran (FIG. 9(A)). After mosquito larvae were fed on normal food without dsRNA (1st control), with the GFP dsRNA-based nanoparticles (2nd control), and with the AgCHS2 dsRNA-based nanoparticles for four days, we exposed the larvae to calcofluor white or dithiothreitol. Both the mortality and percentage of the larvae with a disrupted PM phenotype increased by 29.3% in the larvae fed on the AgCHS2 dsRNA-based nanoparticles as compared with those of the control larvae fed on the GFP dsRNA-based nanoparticles after the larvae were exposed to dithiothreitol at 2.5 mM (FIGS. 9(B), (C)). Similarly, after the larvae were exposed to calcofluor white at 3 and 4 mg/ml, their mortalities increased by 16.7% and 48.0%, respectively, and the percentages of the larvae with a disrupted PM phenotype increased by 31.1% and 24.4%, respectively, in the larvae fed on the AgCHS2 dsRNA-based nanoparticles as compared with those of the control larvae fed on the GFP dsRNA-based nanoparticles (FIGS. 9(D), (E)). The increased larval susceptibility and PM permeability to calcofluor white and dithiothreitol in AgCHS2 dsRNA-fed larvae were due to the reduction of chitin biosynthesis in the midgut. In FIG. 9(B)-(E), all the data are presented as means±SEM of three replications. Different letters on the error bars indicate significant difference based on Fisher's LSD ($P<0.05$).

C. Discussion

The data demonstrates a novel feeding-based RNAi method for mosquito larvae. The innovation of this method is the use of an oral delivery system for mosquito larvae by voluntarily feeding the agarose gel-coated mixture of food and dsRNA that was entrapped in chitosan-based nanoparticles. The use of the nanoparticles may serve two important functions. First, the retention of dsRNA in the nanoparticles in the food gel may be significantly improved in feeding-based RNAi in an aquatic environment. Second, the nanopolymer matrix may dramatically stabilize dsRNA and enhance the efficacy of dsRNA delivery into larval gut epithelial cells. The chitosan/dsRNA nanoparticles may facilitate epithelial uptake of dsRNA through an endocytosis pathway in the gut and enhance the effect of RNAi in mosquito larvae.

The apparent differences in the susceptibility to RNAi in mosquito adults and larvae might be due to either the stability of dsRNA and/or efficacy of cellular uptake of dsRNA. In our laboratory, we made a great effort in larval RNAi by injecting AgCHS1 or AgCHS2 dsRNA into larval bodies of the same mosquito species, but had a very limited success. In contrast, consistent results were obtained when we used this nanoparticle-based approach for RNAi. Thus, our studies suggest that injection is not necessarily more efficient than ingestion for dsRNA delivery although this may be true in some insect species.

The insect CHS1 gene has been known to be exclusively expressed in epidermal and other ectodermal tissues. Indeed, our results supported this notion by showing a high expression of AgCHS1 in the carcass. As the expressions of both AgCHS1 and AgCHS2 can be repressed by the ingestion of AgCHS1 dsRNA in mosquito larvae, the reduction of total chitin content may be not only attributed to the reduction of chitin content in the cuticle and trachea, but also to the reduction of chitin content in the PM. In our study, we tried to stain chitin in the PM by using FITC-conjugated chitin-binding domain (FITC-CBD) but were not able to show much chitin staining in the PM. Because mosquitoes also possess Type 2 PM, it seems that chitin content in Type 2 PM is usually very low. All these suggest that decreased chitin content in mosquito larvae fed on the AgCHS1 dsRNA-based nanoparticles is mainly due to the reduced chitin content in the cuticle and related ectodermal tissues.

Systemic RNAi is a phenomenon of which local administration of dsRNA (e.g., feeding) leads to an RNAi response in whole body through the amplification and spread of silencing to other cells and even to the progenies of an organism. Very limited information on the mechanisms of systemic RNAi in insects is available. To date, it appears that insects lack the RNA-dependent RNA polymerase (RdRP) necessary for driving this RNAi amplification in other organisms. Furthermore, mosquitoes lack not only RdRP but also SID-1, which is required for spreading RNAi responses in *C. elegans*. The success of feeding-based RNAi for AgCHS1 gene which is exclusively expressed in epidermal and related ectodermal tissues in our study strongly suggests a systemic nature of RNAi in mosquito larvae. This notion was mainly based on our results showing significant repression of AgCHS1 gene expression and reduction of chitin content in the larvae carcass while AgCHS1 dsRNA was delivered through larval feeding.

Our nanoparticle-based RNAi method can be applied for functional analysis of genes expressed virtually in any tissue if RNAi is systemic in an insect. Our method also shows considerable potentials for insect control, in which ingestion of dsRNA is often required. For example, reduced chitin content in the cuticle by RNAi of AgCHS1 can enhance the toxicity of diflubenzuron, a benzylphenolurea insecticide that inhibits chitin biosynthesis in insects. Such an RNAi-mediated effect can be potentially used as a strategy to enhance the toxicity of many insecticides for insect pest management.

In insects, the PM is a tubular film composed of proteins, chitin and glycosaminoglycans, and plays important roles in protecting the epithelium from mechanical damage, facilitating food digestion, serving as a barrier of pathogens, and filtration of toxins. Our results indicated that increased larval mortalities in dithiothreitol- or calcofluor white-treated mosquito larvae after RNAi of AgCHS2 were caused by the reduction of chitin content due to the RNAi along with the disruption of chitin-associated proteins due to the chemicals, both leading to the increased permeability of the PM in the larvae. Thus, our results further suggest that silencing of the CHS2 gene by RNAi may serve as a novel strategy for insect pest management.

The present study has proven the concept of using oral RNAi for mosquito control. In addition, our results have shown a great potential for incorporating such a feeding-based RNAi method into a pest management program to increase the efficacy of insecticides. As more genome sequences become available and more potential target genes are identified in insects, development of novel RNAi methods will not only facilitate functional studies of new genes but also revolutionize the technologies for insect pest management.

We claim:

1. A nanoparticle useful for RNAi of a target insect gene, said nanoparticle having a structure comprising:
   a biopolymer matrix; and
   an insect dsRNA that is from about 200 to about 1,000 base pairs in length, wherein said insect dsRNA is entrapped in said biopolymer matrix to thereby form said nanoparticle structure,
   wherein said nanoparticle is prepared by mixing said biopolymer and said dsRNA, wherein said biopolymer and dsRNA self-assemble into said nanoparticle.

2. The nanoparticle of claim 1, wherein said insect dsRNA is bound to said polymer matrix.

3. The nanoparticle of claim 1, wherein said biopolymer is selected from the group consisting of cellulose, chitin, starch, collagen, and derivatives thereof.

4. The nanoparticle of claim 1, wherein said biopolymer is chitosan.

5. The nanoparticle of claim 1, wherein said insect dsRNA comprises a first strand and a second strand, wherein at least one strand comprises a region of complementarity that is substantially complementary to at least a portion of an mRNA transcript of said target insect gene or to at least a portion of an mRNA encoding a protein of said target insect gene.

6. The nanoparticle of claim 5, wherein said target insect gene is a chitin synthase gene.

7. The nanoparticle of claim 5, wherein at least one strand of said dsRNA is a transcript of SEQ ID NO:1, SEQ ID NO:3, or any contiguous portion thereof of at least about 200 nucleotides.

8. The nanoparticle of claim 5, wherein at least one strand of said dsRNA is selected from the group consisting of: a transcript of residues 2,267 to 2,635 of SEQ ID NO: 1; a transcript of residues 3,812 to 4,202 of SEQ ID NO: 1; a transcript of residues 3,846 to 4,235 of SEQ ID NO:3; and a transcript of residues 3,331 to 3719 of SEQ ID NO:3.

9. An insect bait useful for oral administration of dsRNA for RNAi in insects, said bait comprising a nanoparticle and an edible insect attractant dispersed or dissolved in a carrier, said nanoparticle having a structure comprising a biopolymer matrix and insect dsRNA that is from about 200 to about 1,000 base pairs in length, wherein said insect dsRNA is entrapped in said biopolymer matrix to thereby form said nanoparticle structure, and wherein said nanoparticle is prepared by mixing said biopolymer and said dsRNA, wherein said biopolymer and dsRNA self-assemble into said nanoparticle.

10. The insect bait of claim 9, wherein said attractant is selected from the group consisting of sugars, proteins, carbohydrates, fats, yeasts, oils, and mixtures thereof.

11. The insect bait of claim 9, wherein said carrier is selected from the group consisting of agarose, pectin, gelatin, and combinations thereof.

12. The insect bait of claim 9, wherein said bait is in a form selected from the group consisting of liquid, gel, self-sustaining gel-matrix, tablet, granular, and combinations thereof.

13. The insect bait of claim 9, said bait comprising from about 0.1 to about 5% by weight nanoparticles, based upon the total weight of the bait taken as 100% by weight.

14. The nanoparticle of claim 1, wherein said insect dsRNA is bound to said biopolymer through electrostatic interaction, ionic interaction, covalent bonding, or Van der Waals forces.

15. The nanoparticle of claim 1, wherein said insect dsRNA is physically entrapped in said biopolymer matrix.

* * * * *